(12) United States Patent
Demokritou et al.

(10) Patent No.: US 9,360,408 B2
(45) Date of Patent: Jun. 7, 2016

(54) METHODS OF MEASURING EFFECTIVE DENSITY OF NANOPARTICLE AGGLOMERATES DISPERSED IN A LIQUID USING CENTRIFUGATION

(71) Applicant: PRESIDENT AND FELLOWS OF HARVARD COLLEGE, Cambridge, MA (US)

(72) Inventors: Philip Demokritou, Brookline, MA (US); Glen Deloid, Natick, MA (US); Joel Cohen, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/407,649

(22) PCT Filed: Jun. 20, 2013

(86) PCT No.: PCT/US2013/046797
§ 371 (c)(1),
(2) Date: Dec. 12, 2014

(87) PCT Pub. No.: WO2013/192412
PCT Pub. Date: Dec. 27, 2013

(65) Prior Publication Data
US 2015/0140597 A1    May 21, 2015

Related U.S. Application Data

(60) Provisional application No. 61/661,895, filed on Jun. 20, 2012.

(51) Int. Cl.
*G01N 9/36* (2006.01)
*G01N 9/30* (2006.01)
*C12Q 1/02* (2006.01)
*B82Y 35/00* (2011.01)

(52) U.S. Cl.
CPC .. *G01N 9/36* (2013.01); *C12Q 1/02* (2013.01); *G01N 9/30* (2013.01); *B82Y 35/00* (2013.01)

(58) Field of Classification Search
None
See application file for complete search history.

(56) References Cited

U.S. PATENT DOCUMENTS

| | | | |
|---|---|---|---|
| 4,610,846 A | 9/1986 | Martin | |
| 4,927,750 A | 5/1990 | Dorn | |
| 5,188,780 A | 2/1993 | Lange et al. | |
| 5,663,051 A * | 9/1997 | Vlasselaer | B01L 3/5021 210/781 |
| 6,346,421 B1 | 2/2002 | Anderson et al. | |
| 2005/0142206 A1 | 6/2005 | Brown et al. | |
| 2012/0142089 A1 | 6/2012 | Park | |

OTHER PUBLICATIONS

Arnold M. et al. Hydrodynamic Characterization of Surfactant Encapsulated Carbon Nanotubes Using an Analytical Ultracentrifuge. ACS Nano 2(11)2291-2300, Nov. 2008.*
Braun A. et al. Validation of Dynamic Light Scattering and Centrifugal Liquid Sedimentation Methods for Nanoparticle Charterisation. Advanced Powder Technology 22(6)766-770, Nov. 2011.*
Mittal V. Sedimentation Analysis of Organic-Inorganic Hybrid Colloids. Colloid and Polymer Science 288(6)621-630, Apr. 2010.*
PCT International Search Report dated Nov. 22, 2013 for International Application No. PCT/US2013/046797.
Cohen, J. et al., "Interactions of Engineered Nanomaterials in Physiological Media and Implications for in vitro Dosimetry," Nanotoxicology, Early Online, pp. 1-15, 2012.

* cited by examiner

*Primary Examiner* — Ralph Gitomer
(74) *Attorney, Agent, or Firm* — Saul Ewing LLP; Kathryn Doyle; Domingos J. Silva

(57) ABSTRACT

The invention includes a method of determining the effective density of nanomaterial agglomerates in liquids, such as but not limited to physiological fluids, using volumetric centrifugation. The method of the invention allows for the development of reliable and efficient in vitro dosimetry and methods for toxicological testing of engineered nanomaterials.

10 Claims, 8 Drawing Sheets

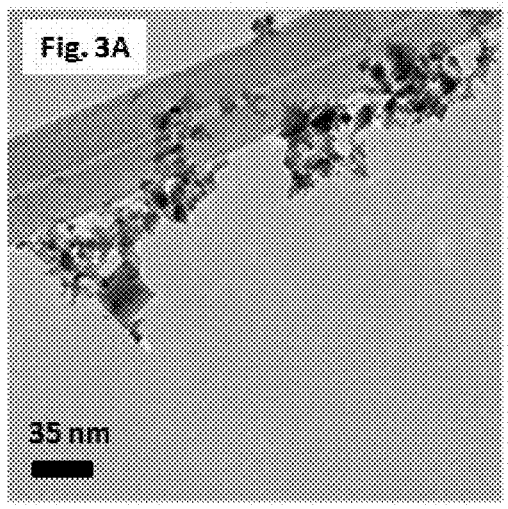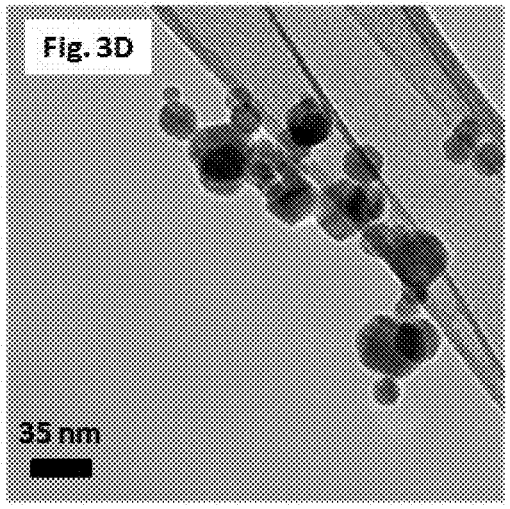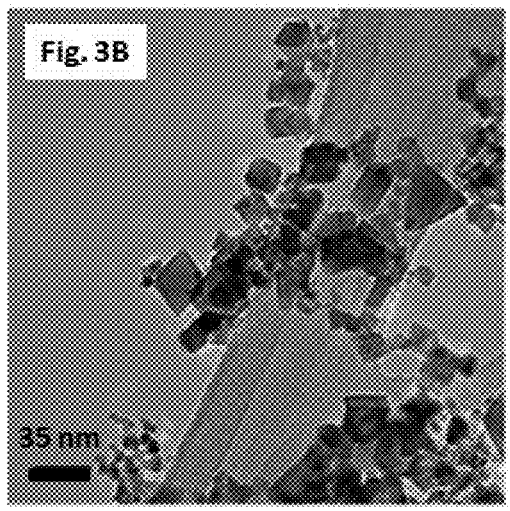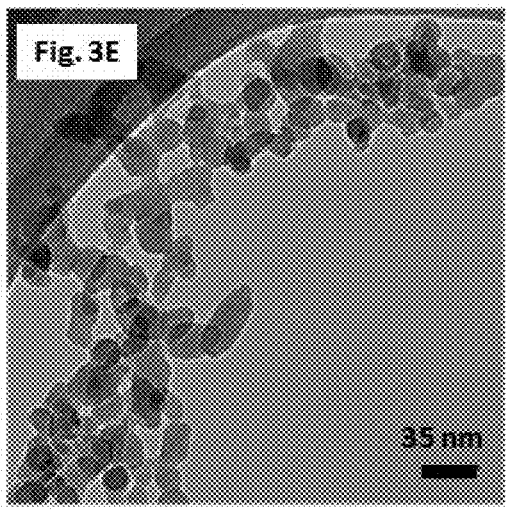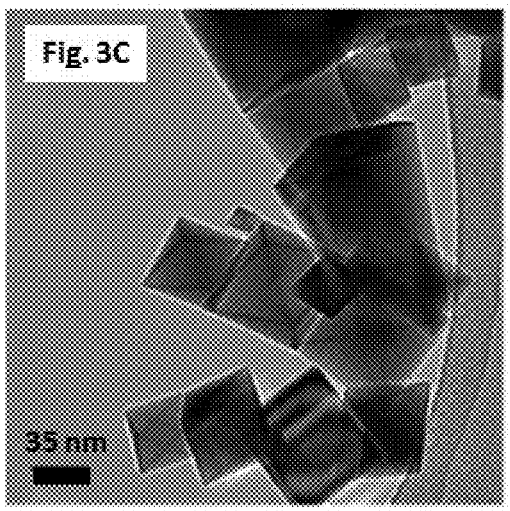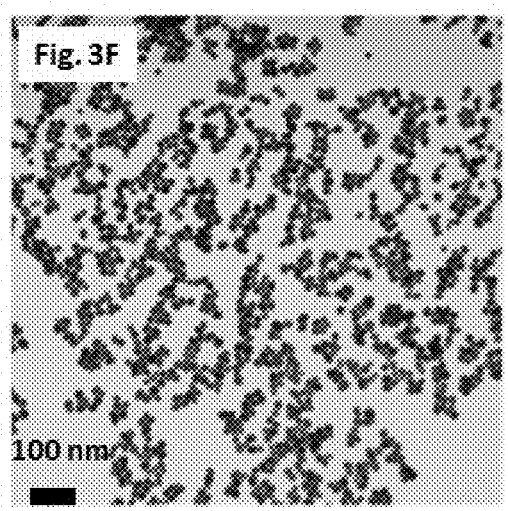

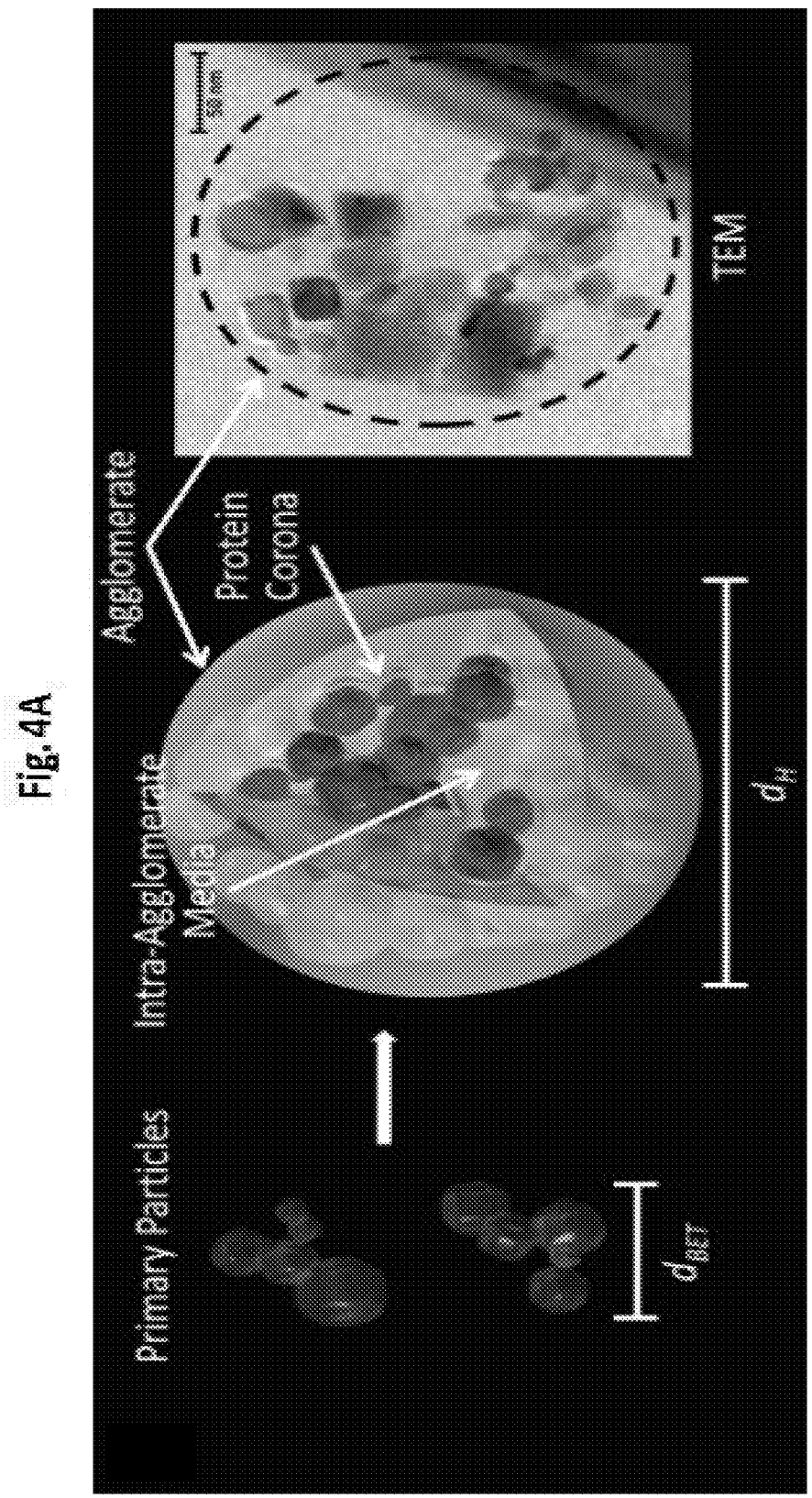

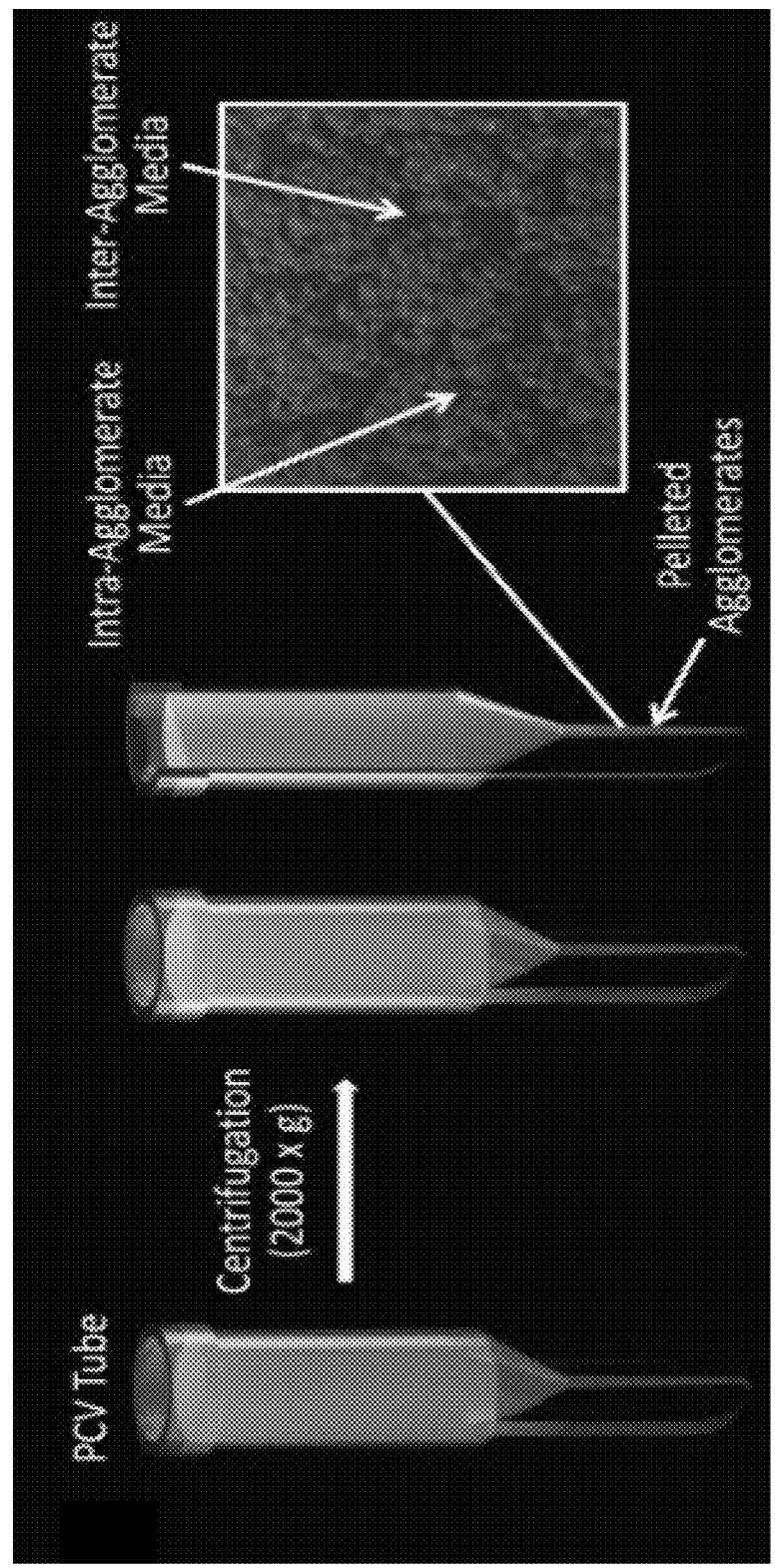

CeO₂ (d_BET=27.9nm)

ZnO (d_BET=63nm)

Model Input: —— Material Density ········ $\rho_{ES}$ — — $\rho_{EV}$

METHODS OF MEASURING EFFECTIVE DENSITY OF NANOPARTICLE AGGLOMERATES DISPERSED IN A LIQUID USING CENTRIFUGATION

CROSS-REFERENCE TO RELATED APPLICATIONS

The present application is a 35 U.S.C. §371 national phase application of, and claims priority to, PCT Application No. PCT/US2013/046797, filed Jun. 20, 2013, which claims priority under 35 U.S.C. §119(e) to U.S. Provisional Application No. 61/661,895, filed Jun. 20, 2012, all of which applications are hereby incorporated by reference in their entireties herein.

STATEMENT REGARDING FEDERALLY SPONSORED RESEARCH OR DEVELOPMENT

This invention was made with government support under grant number ES-0000002 awarded by the National Institute of Environmental Health Sciences (NIH). The government has certain rights in the invention.

BACKGROUND OF THE INVENTION

The physicochemical properties of engineered nanomaterials (ENMs) (such as mobility, quantum size effects, surface area, and surface energy) differ substantially from those of the corresponding bulk materials sharing the same chemical composition and atomic structure. These properties endow ENMs with exceptional conductivity, reactivity and optical sensitivity, and hence superior functionality in consumer products such as sporting goods, tires, catalysts, microelectronics, cleaners, paints, cosmetics and pharmaceuticals. On the other hand, these same properties also result in interactions of ENMs with biological systems that vary from those of their micron-sized counterparts, potentially making nanomaterials unsafe for humans and for the environment (Nel et al., 2006, Science 311:622-627).

The most common exposure pathways for these ENMs include ingestion (e.g., pharmaceutical products and food), dermal contact (e.g., occupational exposure and cosmetics), injection (e.g., nanomedicines and drug delivery mechanisms) and inhalation (e.g., occupational and consumer exposure), potentially resulting in diverse toxicological outcomes. For example, recent studies suggest that inhaled nanoparticles may pass from the lungs into the bloodstream and enter extrapulmonary organs, leading to increased cardiovascular morbidity and mortality (Choi et al., 2010, Nat. Biotechnol. 28:1300-1303; Brain, 2009, Nanotoxicol. 3:7; Mills et al., 2009, Nat. Clin. Pract. Cardiovasc. Med. 6:36-44). Although preliminary evidence demonstrates the potential for ENMs to cause adverse biological effects, the underlying toxicity mechanisms are not currently well understood (Oberdorster, 2007, Nanotoxicol. 1:24).

Attempts have been made to develop efficient and inexpensive screening tools to correlate mechanisms of biological activity and toxicity with ENM characteristics, such as size, shape and surface area (Rallo et al., 2011, Environ. Sci. Technol. DOI: 10.1021/es103606x; Shaw et al., 2008, Proc. Natl. Acad. Sci. USA 105:7387-7392; Krewski et al., 2010, J. Toxicol. Environ. Health B Crit. Rev. 13:51-138). Due to the high cost and time required for in vivo toxicity studies, most of these efforts have focused on in vitro methods (Lai, 2011, Nanomed. Nanobiotechnol. DOI:10.1002/wnan.162; Balbus et al., 2007, Environ. Health Perspect. 115:1654-165). High-throughput in vitro toxicity assays have recently been employed to assess toxicity end points, in various cell lines, for libraries of ENMs over a range of exposure times and concentrations (George, 2011, ACS Nano 5:13).

In addition to the refinement and standardization of in vitro and in vivo methods, delivery of ENMs in liquid suspension to cultured cells (a typical procedure in in vitro toxicity studies) requires further analysis. First, commercial ENM nanopowders have limited diversity in terms of physicochemical and morphological properties, hampering the systematic parametric study of the relationships between biological outcomes and ENM properties (such as size, surface, composition, shape, and charge). Second, ENMs suspended in culture media may flocculate, agglomerate, dissolve, or even interact with serum components (Fadeel, 2010, Adv. Drug Deliv. Rev. 8:9; Jones & Grainger, 2009, Adv. Drug Deliv. Rev. 61:438-456; Verma & Stellacci, 2010, Small 6:12-21), thus assuming distinct biological properties. More importantly, administered doses may differ substantially from the doses actually delivered to cells. Comparison of in vitro doses to those administered by inhalation is difficult, resulting in large differences in effective dose between in vitro and in vivo studies. Taken together, these limitations may explain some of the disparities reported in the literature between in vivo and in vitro ENM studies (Fadeel, 2010, Adv. Drug Deliv. Rev. 8:9; Fischer & Chan, 2007, Curr. Opin. Biotechnol. 18:565-571).

Typical comparisons of biological response to ENM exposure do not take into account particle-particle and particle-physiologic fluid interactions in the liquid suspension (Oberdorster et al., 2005, Environ. Health Perspect. 113:823-839; Jiang, 2008, Nanotoxicol. 2:10; Rushton et al., 2010, J. Toxicol. Environ. Health A 73:445-461; Wittmaack, 2007, Environ. Health Perspect. 115:8; Oberdorster et al., 1994, Environ. Health Perspect 102(Suppl. 5):173179). Such interactions depend largely on the dispersion protocol; the particle characteristics (including primary particle size and shape, chemical composition and surface chemistry) (Ji et al., 2010, Environ. Sci. Technol. 44:7309-7314; Jiang, 2009, J. Nanopart. Res. 11:13; Murdock et al., 2008, Toxicol. Sci. 101:239-253; Zook et al., 2010, Nanotoxicol. DOI: 10.3109/17435390.2010.536615); and the liquid media properties (such as ionic strength, specific conductance, pH and protein content) (Lee et al., 2011, J. Comp. Neurol. 519:34-48; Bihari et al., 2008, Part. Fibre Toxicol. 5:14; Elzey, 2009, J. Nanopart. Res. 12:14; Murdock et al., 2008, Toxicol. Sci. 101:239-253; Zook et al., 2010, Nanotoxicol. DOI: 10.3109/17435390.2010.536615; Wiogo et al., 2011, Langmuir 27:843-850; Laxen, 1977, Water Res. 11:4).

ENM interactions, in turn, lead to agglomeration in liquid media, altering the total number of free particles in suspension and the total surface area available for interaction with cells in vitro, as well as the mass transport of ENMs (i.e., sedimentation and diffusion coefficients), which directly impacts delivery of particles to cells (Teeguarden et al., 2007, Toxicol. Sci. 95:300-312). For example, rapidly settling particles elicit cytokine secretion within minutes of application, whereas slow or non-settling particles may take several hours to elicit a similar response (Teeguarden et al., 2007, Toxicol. Sci. 95:300-312). Further, the methods used to disperse nanoparticles in culture media for in vitro studies, which can substantially affect their physical and chemical properties—and hence their biological activities—differ widely (Roco, 2011, J. Nanoparticle Res. 13(3):897-919). Clearly a harmonized (standardized and shared) protocol for nanoparticle dispersion is required to ensure that congruous and cumulative data become available.

The extent of agglomeration of ENMs in a fluid may be controlled by adopting dispersion protocols that include identification of the critical dispersion energy needed to generate the smallest possible agglomerate sizes and distributions that are optimally stable over time (Cohen et al., 2012, Nanotoxicol. doi:10.3109/17435390.2012.666576; Taurozzi, "Protocol for Preparation of Nanoparticle Dispersions from Powdered Material Using Ultrasonic Disruption", CEINT/NIST, 2010; Taurozzi et al., 2012, Nanotoxicol. doi:10.3109/17435390.2012.665506). In addition to a stable and well-characterized suspension, accurate modeling of ENM transport requires accurate calculation of agglomerate size and shape, as well as the heretofore elusive property of density.

Particle transport in static uniform solutions at constant temperature (conditions inherent to in vitro systems) is primarily driven by diffusion and sedimentation (Teeguarden et al., 2007, Toxicol. Sci. 95(2):300-12; Cho et al., 2011, Nat. Nanotechnol. 6(6):385-91; Hinderliter et al., 2010, Part. Fibre Toxicol. 7(1):36). For the purposes of modeling particle transport in an in vitro system, diffusion and sedimentation velocities can be estimated based on the following equations. The Stokes-Einstein equation defines the diffusion coefficient (D, m$^2$/s) as:

$$D = \frac{k_B T}{3\pi \mu d} \quad (1)$$

where $k_B$ is the Boltzmann constant (Pa·m$^3$·K$^{-1}$), $\mu$ is the media dynamic viscosity (Pa·s), and d is the particle diameter (m) in suspension.

The sedimentation velocity of a particle in suspension, derived from the frictional drag force (defined by Stokes' Law), buoyant force and gravitational force acting upon it is defined as $$v = \frac{g(\rho_E - \rho_{media})d^2}{18\mu}, \quad (2)$$

where g is acceleration due to gravity (m/s$^2$), $\rho_E$ is particle effective density (g/cm$^3$), $\rho_{media}$ is media density (g/cm$^3$), d is the diameter of the particle in solution (m), and $\mu$ is the media viscosity (Pa·s).

From these equations, it is clear that agglomeration can influence particle transport by altering particle size, as well as by altering particle effective density. Typically, ENM agglomerates in liquid suspension are not composed of efficiently packed particles with zero porosity and do not have densities equal to that of the raw material ($\rho_p$). Rather, ENMs exhibit "chain like" fractal structures and are porous, resulting in the formation of protein coronas and entrapment of liquid media within the agglomerate. As a result, the effective density of the resulted agglomerate, ($\rho_E$), can be significantly lower than that of the raw material ($\rho_p$), and may be closer to the density of the media ($\rho_{media}$).

Current methods for empirically measuring the effective density of ENM agglomerates in liquid suspension are time consuming and require specialized and expensive equipment. Analytical ultracentrifugation measurements can take up to several days per sample and often fail due to samples leaking from cell housing units, making characterization of a large panel of ENMs a prolonged and expensive endeavor (Schulze et al., 2008, Nanotoxicology 2(2):11; Mittal & Lechner, 2010, J. Colloid Interface Sci. 346(2):378-83; Zook et al., 2011, ACS Nano 5(10):8070-9). Other studies have reported and based modeling and dose calculations on effective densities estimated from complex models that rely on best-guess values for a number of ENM-specific parameters, including the number of particles per agglomerate, the specific fractal dimension of the ENM (DF) and packing factor (PF) (Cohen et al., 2012, Nanotoxicol. doi:10.3109/17435390.2012.666576; Hinderliter et al., 2010, Part. Fibre Toxicol. 7(1):36). The fractal dimension contributes substantially to the broad hypothetical range of ENM effective density, having values between 1 and 3, where a value of 3 indicates a perfect compact sphere with zero porosity. Packing factor values contribute additional uncertainty, theoretically varying from 0 to 1, where a value of 1 indicates agglomerates are efficiently packed with zero porosity (Hinderliter et al., 2010, Part. Fibre Toxicol. 7(1):36; Sterling et al., 2005, Water Res. 39(9):1818-30). The ENM-specific values for DF and PF are not well known and have not been validated in experimental studies. For metal oxides, estimated best-guess values of 2.3 and 0.637 for DF and PF, respectively, have been used in the literature (Cohen et al., 2012, Nanotoxicol. doi: 10.3109/17435390.2012.666576; Hinderliter et al., 2010, Part. Fibre Toxicol. 7(1):36; Sterling et al., 2005, Water Res. 39(9):1818-30).

From the foregoing discussion, it is clear that there is a need in the art for methods that allow empirical measurement of effective density of ENM agglomerates in liquid suspension. Such methods could be used to correlate ENM properties with their biological activity and toxicity. The present invention addresses this need.

BRIEF SUMMARY OF INVENTION

The invention includes a method of determining the effective density of a nanomaterial agglomerate in a liquid. The method comprises providing a dispersion of the nanomaterial agglomerate in the liquid. The method further comprises centrifuging the dispersion at a speed sufficient to yield a supernatant and a pellet, wherein the pellet comprises a fraction of the nanomaterial agglomerate. The method further comprises measuring the volume of the pellet. The method further comprises using the volume of the pellet to determine the effective density of the nanomaterial agglomerate.

In one embodiment, the speed of centrifugation is equal to or less than about 6,000×g. In another embodiment, the speed of centrifugation is equal to or less than about 2,000×g. In yet another embodiment, the dispersion is centrifuged for about 1 hour or less. In yet another embodiment, the dispersion is centrifuged for about 3 hours or less. In yet another embodiment, the dispersion is centrifuged for about 1 hour or less.

In one embodiment, the mass of nanomaterial agglomerate is greater in the pellet than in the supernatant. In another embodiment, the ratio of mass of nanomaterial agglomerate in the pellet and the supernatant is equal to or greater than about 96:4. In yet another embodiment, the nanoparticles stack as tight ordered spheres in the pellet. In yet another embodiment, the stacking factor for the nanoparticles is about 0.74048.

In one embodiment, the effective density of the nanomaterial agglomerate is used to determine the amount of time required for a given amount of the nanomaterial agglomerate initially dispersed in the liquid to sediment. In another embodiment, the effective density of the nanomaterial agglomerate is used to determine the amount of time required for a given amount of the nanomaterial agglomerate initially overlaying a cell to sediment upon the cell and thus be delivered to the cell. In yet another embodiment, the effective density of the nanomaterial agglomerate is used to determine the amount of nanomaterial agglomerate initially dispersed in the liquid that sediments within a given period of time. In yet another embodiment, the effective density of the nanomaterial agglomerate is used to determine the amount of nanomaterial agglomerate initially dispersed in the liquid that is deposited upon a cell when the dispersion overlays the cell for a given period of time.

In one embodiment, the amount of nanomaterial agglomerate that sediments is a given percentage of the mass of the nanomaterial agglomerate initially dispersed in the liquid. In another embodiment, the given percentage is about 90%. In yet another embodiment, the amount of nanomaterial agglomerate that sediments is a given percentage of the mass of the nanomaterial agglomerate initially dispersed in the liquid. In yet another embodiment, the given percentage is about 90%. In yet another embodiment, the liquid comprises a biological fluid.

The invention further includes a kit for determining the effective density of a nanomaterial agglomerate in a liquid. In one embodiment, the kit comprises a centrifuge tube and an instructional material for use thereof, wherein the kit optionally comprises the liquid. In another embodiment, the instructional material recites at least the following method steps: providing a dispersion of the nanomaterial agglomerate in the liquid; centrifuging the dispersion in the centrifuge tube at a speed sufficient to generate a supernatant and a pellet, wherein the pellet comprises a fraction of the nanomaterial agglomerate; measuring the volume of the pellet generated; and using the volume of the pellet generated to determine the effective density of the nanomaterial agglomerate.

In one embodiment, the centrifuge tube comprises a packed cell volume (PCV) tube. In another embodiment, the PCT tube is equipped with a volumetric pellet capturing capillary.

BRIEF DESCRIPTION OF THE DRAWINGS

The following detailed description of preferred embodiments of the invention is better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1A: VENGES $SiO_2$ ($d_{BET}$=18.6 nm). FIG. 1B: $CeO_2$ ($d_{BET}$=71.3 nm). FIG. 1C: CuO ($d_{BET}$=58 nm). FIG. 1D: Gold nanospheres ($d_H$=42.2 nm).

FIGS. 3A-3F illustrate TEM images of representative ENMs in raw powder form. FIG. 3A: $CeO_2$ ($d_{BET}$=5.4 nm). FIG. 3B: $CeO_2$ ($d_{BET}$=23.7 nm). FIG. 3C: $CeO_2$ ($d_{BET}$=119 nm). FIG. 3D: $SiO_2$ ($d_{BET}$=18.6 nm). FIG. 3E: $Fe_2O_3$ ($d_{BET}$=27.6 nm). FIG. 3F: Gold nanospheres ($d_H$=42.2 nm).

FIGS. 4A-4C illustrates agglomeration of ENMs, transport in culture and volumetric centrifugation. FIG. 4A is a schematic illustration of the finding that ENM primary particles suspended in cell culture media exist as agglomerates consisting of multiple primary particles, which may be enveloped by a corona of proteins from the media, and media trapped between primary particles (intra-agglomerate media). FIG. 4B is a schematic illustration of the finding that ENM agglomerates within suspensions applied to cells settle toward the cells over time as a result of mass transport (sedimentation and diffusion). The initial administered dose is the concentration of ENM in the initially homogeneous suspension. As transport progresses agglomerates are concentrated near or deposited onto the cells. The mass of ENM deposited per area is the delivered dose. FIG. 4C is a schematic illustration of the finding that in volumetric centrifugation a sample of ENM suspension is centrifuged in a packed cell volume (PCV) tube to produce a pellet, the volume of which can be used to estimate the effective density of the ENM in suspension. The pellets contain both packed agglomerates and the media remaining between them (inter-agglomerate media). The fraction of the pellet volume occupied by agglomerates may be referred to as the stacking factor (SF).

FIG. 5A: $CeO_2$ ($d_{BET}$=27.9 nm), FIG. 5B: ZnO ($d_{BET}$=63 nm). The dotted and dashed lines represent deposition based on densities determined by volumetric centrifugation and the Sterling method, respectively.

DETAILED DESCRIPTION OF THE INVENTION

Figure 1:
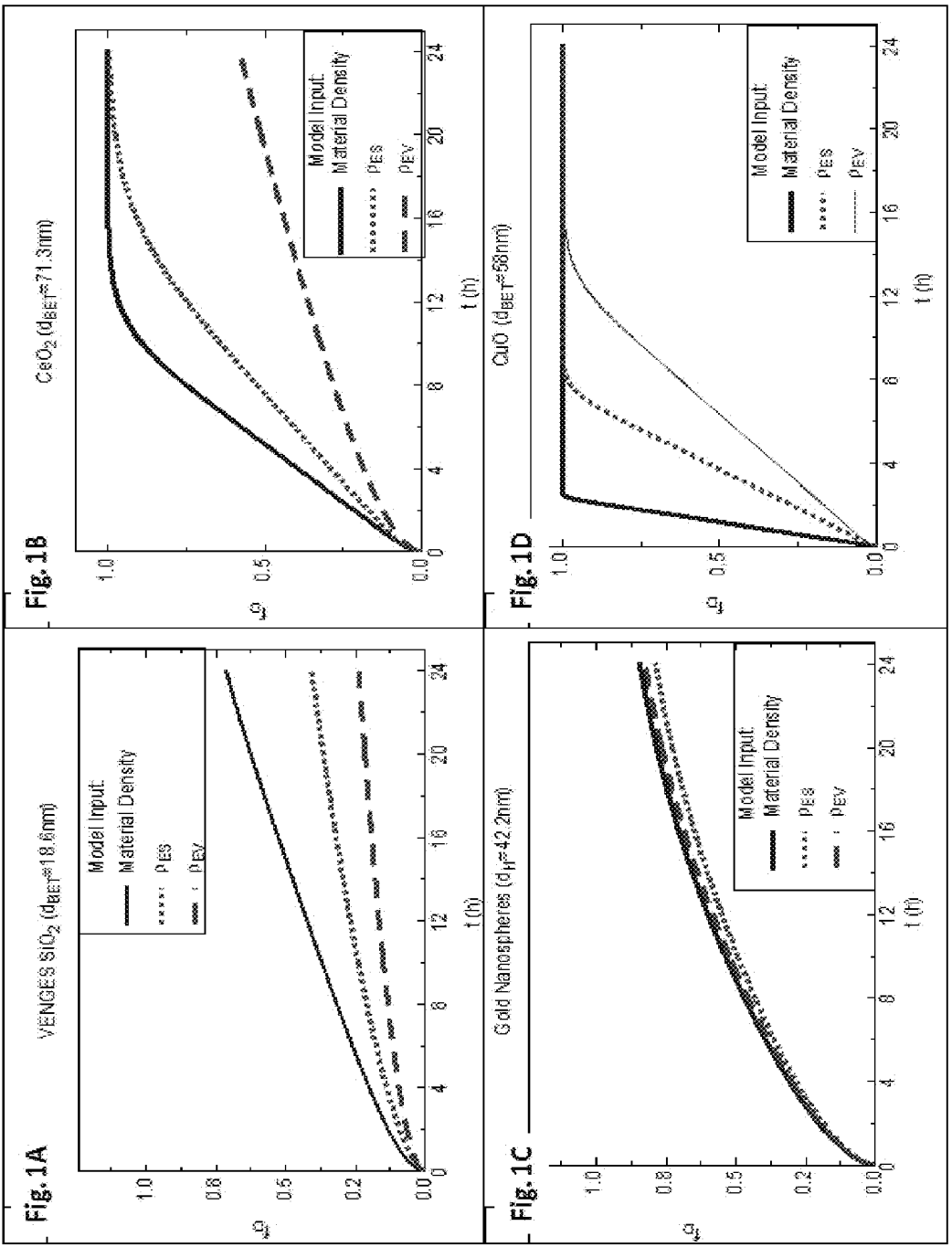
FIGS. 1A-1D are a series of graphs illustrating the fraction of administered dose deposited, $f_D$, as a function of time (in hours) for ENMs calculated using either the material density, Sterling estimated effective density ($\rho_{ES}$), or volumetrically estimated effective density ($\rho_{EV}$).

The present invention relates to the unexpected discovery of simple and novel methods to estimate the effective density of ENM agglomerates in liquid suspension. Effective density is an important determinant of in vitro dosimetry, and the methods of the invention are thus useful for improving the accuracy of in vitro dosimetric numerical models and helping understand nanobiointeractions at the cellular level. The methods of the invention are not limited to biological systems or biointeractions, and may be applied to any area where nanoparticles are used, such as, but not limited to, nanoengineering and material science in general.

DEFINITIONS

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

As used herein when referring to a measurable value such as an amount, a temporal duration, and the like, the term "about" is meant to encompass variations of ±20% or ±10%, more preferably ±5%, even more preferably ±1%, and still more preferably ±0.1% from the specified value, as such variations are appropriate to perform the disclosed methods.

As used herein, the term "AUC" refers to analytical ultracentrifugation.

As used herein, the term "ENM" refers to engineered nanomaterial.

As used herein, the term "PCV" refers to packed cell volume.

As used herein, the term "TEM" refers to transmission electron microscopy.

As used herein, the term "DLS" refers to dynamic light scattering.

As used herein, the term "SSA" refers to specific surface area.

As used herein, the term "SF" refers to stacking factor.

The term "fluid" or "liquid" as used herein includes a biological fluid obtained from a patient, such as, but not limited to, blood, lymph, urine, spinal or synovial fluid, or a fluid obtained from any organ or region of the body. A fluid may also include a non-clinical fluid or liquid, such as a solution or liquid obtained from a non-clinical source, such as an organic or inorganic fluid. In one embodiment, the fluid is aqueous. In another embodiment, the fluid is not aqueous.

As used herein, an "instructional material" includes a publication, a recording, a diagram, or any other medium of expression that can be used to communicate how to use the kit of the invention. Optionally, or alternately, the instructional material can describe one or more methods of for use of the kit of the invention. The instructional material of the kit of the invention can, for example, be affixed to a container that contains the kit, or be shipped together with a container that contains the kit. Alternatively, the instructional material can be shipped separately from the container with the intention that the instructional material and the kit be used cooperatively by the recipient.

The terms "patient," "subject," and "individual" are used interchangeably herein, and refer to any animal, or cells thereof whether in vitro or in situ, amenable to the methods described herein. Preferably, the patient, subject or individual is a mammal, and more preferable, a human.

The term "treatment" as used within the context of the present invention is meant to include therapeutic treatment as well as prophylactic, or suppressive measures for the disease or disorder. Thus, for example, the term "treatment" includes the administration of an agent prior to or following the onset of a disease or disorder thereby preventing or removing all signs of the disease or disorder. As another example, administration of the agent after clinical manifestation of the disease to combat the symptoms of the disease comprises "treatment" of the disease.

As used herein, a "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

DESCRIPTION

Discrepancies in the nanotoxicology literature, where ENM properties fail to correlate with their biological activity, may be attributed to inadequate characterization of ENMs in suspension and subsequent particle delivery to adherent cells. Specifically, the formation of protein coronas and incorporation of the suspending liquid media in agglomerates reduces the effective density of ENMs, thereby reducing the rate of particle delivery to cells and complicating dosimetry issues.

Addressing this need, the present invention includes a simple and novel method of estimating the effective density of ENM agglomerates in liquid suspension based on an empirical measurement. As described herein, the method of the present invention was used to investigate a panel of ENMs (comprising a panel of well-characterized metal and metal oxides) dispersed in physiological fluids commonly used for in vitro toxicity studies. In one embodiment, ENM suspensions were centrifuged in a centrifuge tube, such as but not limited to a packed cell volume (PCV) tube equipped with a volumetric pellet capturing capillary. Effective densities were then determined from the total volume of the ENM pellet, mass of suspended ENMs, and the densities of the ENM raw material and suspension media. The effective densities obtained by this method and the agglomerate diameters obtained by DLS were then used to model ENM delivery to cells in an in vitro system.

The present method for estimating the effective density of ENM agglomerates, based upon empirical measurements of ENM agglomerates pelleted by volumetric centrifugation, is relatively fast, cheap, and does not require estimation of the number of particles per agglomerate, particle fractal dimension, or intra-agglomerate packing factor. As demonstrated herein, the disclosed protocol was applied to a panel of particles generated by various methods for a range of applications, and of varied primary particle sizes, shape, and surface chemistry. With the exception of non-agglomerating gold nanospheres (the effective density of which was close to that of elemental gold), the effective densities of all ENMs in the panel were substantially less than those of the corresponding raw materials, approaching the density of the suspending liquid medium due to formation of agglomerates and protein coronas. Small differences in effective density were observed for the ENMs, and such differences correlated with material density ($CeO_2 > CuO > ZnO > Fe_2O_3 > TiO_2 > SiO_2$). Effective density was found to greatly influence the particle delivery to cells, with implications for in vitro dosimetry and nanotoxicology—effective density can slow particle sedimentation in in vitro systems to the degree that it would take 100+ hours to deliver 90% of an administered dose of ENMs. The method of the invention thus allows for improvements in the accuracy of in vitro dosimetric numerical models and helps understand nanobiointeractions at cellular level.

The results present herein emphasize the powerful influence of effective density on particle mobility and delivery to cells in an in vitro system. Inadequate characterization of ENM transformations in liquid suspension can lead to inaccurate reporting of dose response curves that do not reflect the significant time required to deliver administered doses to cells. This may explain some of the discrepancies reported in the literature for in vitro toxicity of various ENMs, and may have implications for matching toxic doses observed in vitro with those observed in vivo. Thus, accurate estimates for delivered dose must take into account the effective density of ENM agglomerates in liquid suspension, and dose metrics based on accurate transport models may be more physiologically relevant than traditionally reported administered doses. The results presented herein may be extended to dose metrics for additional industrially relevant ENMs, including carbon based materials such as fullerenes and carbon nanotubes, and aim to determine biologically accurate dose response curves for in vitro toxicity.

In one embodiment, the effective density of the nanomaterial agglomerate is used to determine the amount of time required for a given amount of the nanomaterial agglomerate dispersed in the liquid to sediment.

In one embodiment, the effective density of the nanomaterial agglomerate is used to determine the amount of time required for a given amount of the nanomaterial agglomerate dispersed in the liquid overlaying the cells to sediment and thereby be delivered to the cells.

In one embodiment, the effective density of the nanomaterial agglomerate is used to determine the amount of nanomaterial agglomerate dispersed in the liquid that sediments within a given period of time.

In one embodiment, the effective density of the nanomaterial agglomerate is used to determine the amount of nanomaterial agglomerate dispersed in the liquid that is delivered to a cell when the dispersion is contacted with the cell for a given period of time.

In one embodiment, the amount of nanomaterial agglomerate that sediments is a given percentage of the mass of the nanomaterial agglomerate initially dispersed in the liquid. In another embodiment, the amount of nanomaterial agglomerate that sediments is about 50% of the mass of the nanomaterial agglomerate initially dispersed in the liquid. In yet another embodiment, the amount of nanomaterial agglomerate that sediments is about 90% of the mass of the nanomaterial agglomerate initially dispersed in the liquid. In yet another embodiment, the amount of nanomaterial agglomerate that sediments is about 95% of the mass of the nanomaterial agglomerate initially dispersed in the liquid.

The results presented herein demonstrated that accurate assessment of effective density has important implications for in vitro dosimetry, and should be central to the design and interpretation of cellular toxicological studies of ENMs. The importance of accurately determining and accounting for effective density when estimating particle dose actually delivered to cells was also demonstrated, and disregard of this consideration may explain many discrepancies in the nanotoxicology literature. Furthermore, it is critical that in vitro toxicity protocols employ relevant exposure times derived from fully characterized ENM-specific particle-kinetics. In one embodiment, evaluation of toxicity to cells based on delivered dose metrics illustrates the importance of accurate determination of delivered dose, and therefore of effective density, upon which determination of delivered dose largely depends, in assessing the cellular toxicity of ENMs. The results reported herein show the potential of accurate density measurement to improve the consistency and validity of in vitro toxicity evaluations.

Kits of the Present Invention

The present invention further includes a kit containing materials for the determination of effective densities of nanoparticles.

In one embodiment, the kit includes a centrifuge tube that allows for the determination of the volume of the pellet obtained by centrifuging the nanomaterial agglomerate dispersed in a liquid. In one embodiment, the centrifuge tube comprises a packed cell volume (PCV) tube equipped with a volumetric pellet capturing capillary.

In one embodiment, the kit comprises a fluid that may be used to disperse the nanomaterial agglomerate of interest. In another embodiment, the fluid comprises a biological fluid, such as but not limited to serum, blood, urine, saliva, lymph, spinal fluid, synovial fluid, or a fluid obtained from any organ or region of the body. In yet another embodiment, the fluid comprises an organic solvent. In yet another embodiment, the fluid comprises an aqueous buffer.

In one embodiment, the kit includes a nanomaterial agglomerate of known effective density in a specific fluid, wherein this nanomaterial agglomerate may be used as a standard for the implementation and processing of the methods of the invention. In another embodiment, the kit includes a transfer pipet. In yet another embodiment, the kit includes instructions for the use thereof in conjunction with a centrifuge. Additionally, the kit of the invention may include novel software developed to assist and automate the methods of the invention.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Nanomaterials Used in the Study and Characterization of ENM Powders

ENMs investigated in this study are listed in Table 1, and include ENMs generated by various methods for distinct applications, and of varied primary particle size, shape, and surface chemistry.

Industry-relevant metal oxides ($SiO_2$, $Fe_2O_3$, and $CeO_2$) were generated in-house by flame spray pyrolysis using the Harvard Versatile Engineered Nanomaterial Generation System (VENGES) as previously described (Demokritou et al., 2010, Inhal. Toxicol. 22 Suppl 2:107-16; Sotiriou et al., 2011, Nanotoxicol. doi:10.3109/17435390.2011.604439). Additional metal oxide nanoparticles were purchased from commercial vendors ($SiO_2$ and $TiO_2$: EVONIK, Essen, Germany; CuO: Sigma Aldrich, St Louis, Mo.; ZnO: Alfa Aesar, Ward Hill, Mass.).

Spherical monodisperse gold nanospheres developed for biomedical applications were donated by Dr. Srinivas Sridhar at Northeastern University. These particles were used as a reference ENM of known shape and without a chain-like fractal morphology. Nanospheres were prepared by methods previously described with slight modification (Grabar et al., 1995, Anal. Chem. 67:9; Zhu et al., 2003, Langmuir 19:8). Briefly, 500 ml of 1 mM $HAuCl_4$ were taken in a round bottom flask, and the solution was stirred vigorously under heating to bring the solution to rolling boil. 50 ml of 38.8 mM sodium citrate solution were added rapidly to the boiling $HAuCl_4$ solution. A color change from pale yellow to purple indicated the formation of gold nanoparticles. Boiling was further continued for another 15 min, after which the heating source was removed and the solution was further stirred for another 15 min. The solution was filtered through 0.45 μm syringe filters to remove any dust particles or impurities present in the solution. The filtered solution was stored at 4° C. for further use.

Specific Surface Area

Specific surface area (SSA), defined as the particle surface area per mass ($m^2/g$), was determined by the nitrogen adsorption/Brunauer-Emmett-Teller (BET) method (Micrometrics Tristar Norcross, Ga., USA) for each ENM.

The equivalent primary particle diameter, $d_{BET}$, was calculated, assuming spherical particles, as:

$$d_{BET} = \frac{6}{SSA \times \rho_P}$$

where $\rho_p$ is the particle density (obtained for each particle from the densities of component materials, at 20° C., reported in the CRC handbook of Chemistry and Physics; Haynes, 2012, CRC Handbook of Chemistry and Physics, $92^{nd}$ edition).

Particle diameter was also determined by X-ray diffraction and reported as $d_{XRD}$ (nm) (XRD, Bruker D8 Advance, Cu $K_\infty$ Switzerland). Particle morphology and size were further characterized by scanning and transmission electron microscopy (SEM/TEM).

Gold nanoparticles were characterized by measuring the plasmon resonance peak. A typical absorbance at $\lambda_{max}$ 527 nm showed the plasmon peak for the gold nanoparticles (data not shown). The size of the gold nanoparticles was confirmed with Transmission Electron Microscopy (TEM) as well as Dynamic Light Scattering (DLS) measurements.

ENM Dispersal and Characterization in Liquid Suspensions

Dispersions were prepared using a protocol previously developed (Cohen et al., 2012, Nanotoxicol. doi:10.3109/17435390.2012.666576), and included the calibration of sonication equipment and standardized reporting of sonication energy. Sonication was performed in deionized water (DI $H_2O$) to minimize reactive oxygen species generation via sonolysis, to minimize ionic strength and specific conductance (and hence particle interactions) during sonication, and to avoid denaturation of proteins in the final cell delivery media. The critical DSE ($DSE_{cr}$) was determined as previously described for each ENM in order to achieve stable monodisperse suspensions of small agglomerates (Cohen et al., 2012, Nanotoxicol. doi:10.3109/17435390.2012.666576).

ENMs were dispersed at 5 mg/ml in 3 ml of solute in 15 ml, conical polyethylene tubes, using a Branson Sonifier S-450A (Branson Ultrasonics, Danbury, Conn.) fitted with a 3-inch cup horn (maximum power output of 400 W at 60 Hz, continuous mode, output level 3). The tube was immersed so that the sample liquid meniscus was aligned with that of the water in the cup. The system was calibrated by the calorimetric calibration method previously described (Cohen et al., 2012, Nanotoxicol. doi:10.3109/17435390.2012.666576; Taurozzi et al., 2010, Nanotoxicol. doi:10.3109/17435390.2012.665506), whereby the power delivered to the sample was determined to be 1.75 W. Stock solutions in DI $H_2O$ were then diluted to desired concentrations (50 μg/ml, 100 μg/ml, or 250 μg/ml) in either RPMI or F12K cell culture media, each either alone or supplemented with 10% heat inactivated fetal bovine serum, and vortexed for 30 seconds. Dispersions were analyzed for hydrodynamic diameter ($d_H$), polydispersity index (PdI), zeta potential (ζ), and specific conductance (σ) by DLS using a Zetasizer Nano-ZS (Malvern Instruments, Worcestershire, UK). pH was measured using a VWR sympHony pH meter (VWR International, Radnor, Pa., USA).

Effective ENM Density in Liquid Suspensions

Figure 4B:
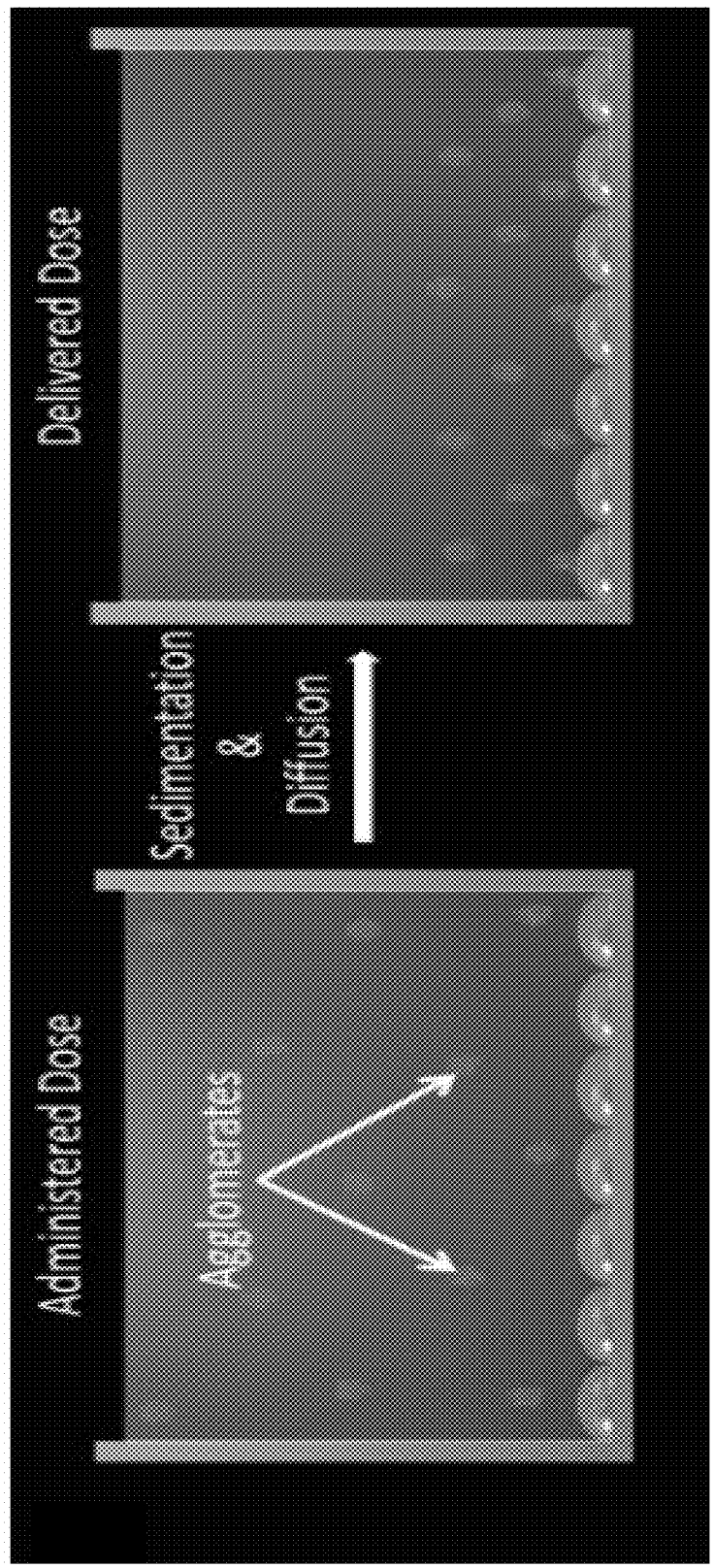
Figure 5A:
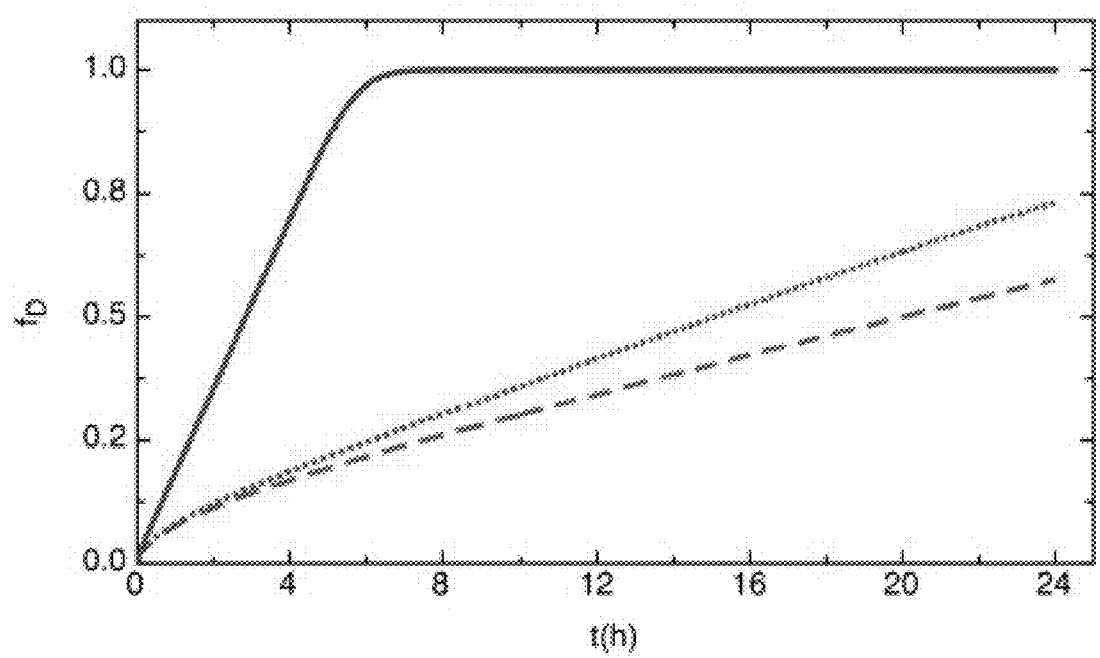
FIGS. 5A-5B are a series of graphs illustrating the role of effective density in the rate of ENM deposition. Modeling of transport over time demonstrated the important role of ENM density in determining the rate of ENM deposition, indicated here by $f_D$, the fraction of the administered dose (total mass of ENM in suspension) deposited at a given time. Assuming a density equal to that of the raw material (solid lines) results in an overestimation of deposition rate to a degree that depends upon the tendency of the ENM to form agglomerates that contain trapped media. Deposition rate curves are shown for selected ENMs investigated suspended in cell culture media typically used for in vitro nanotoxicology study (RPMI/10% FBS).
Figure 5B:
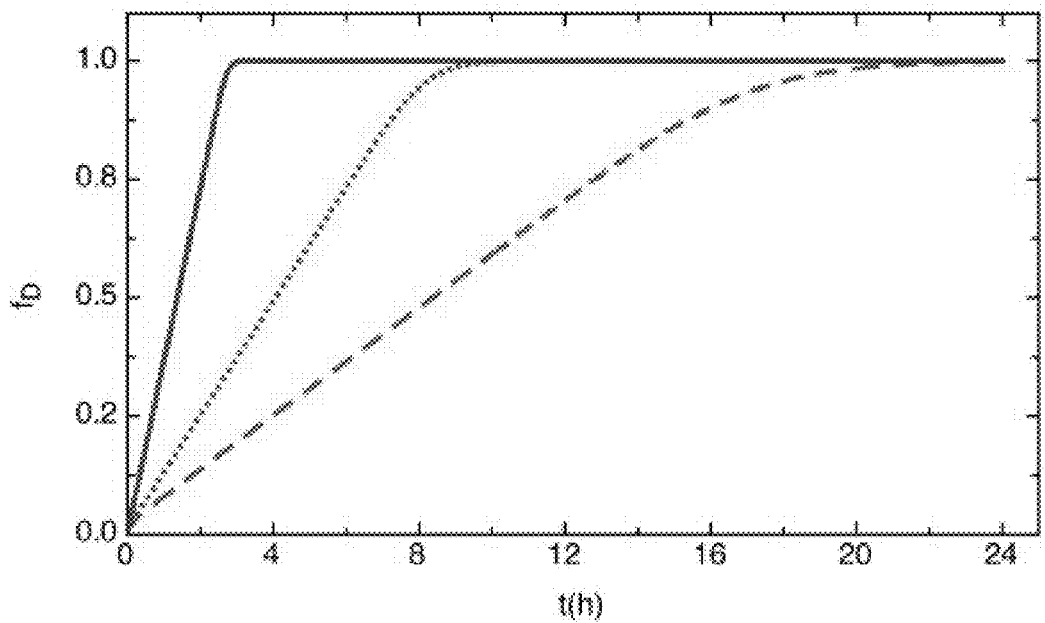
Figure 6:
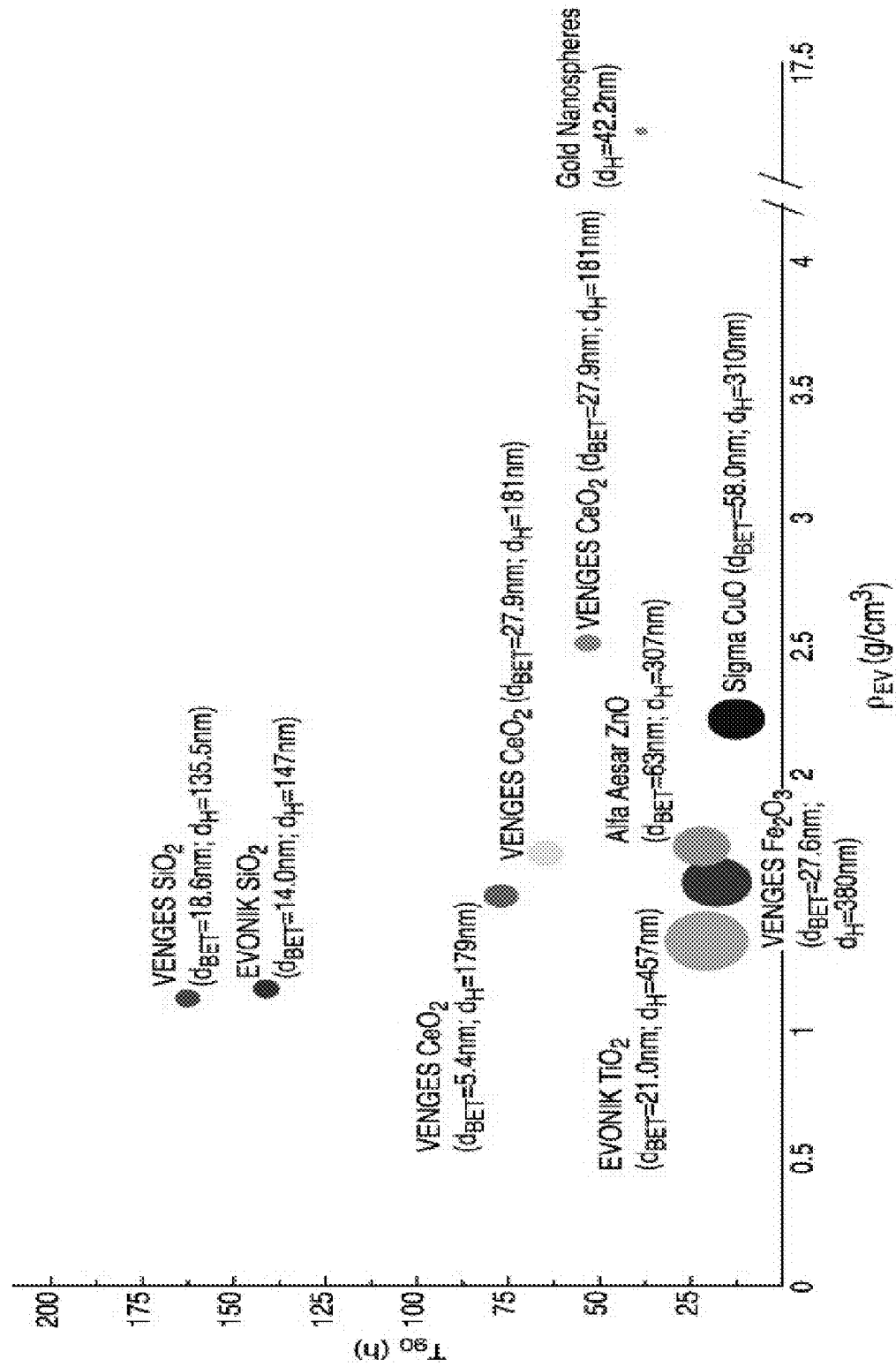
FIG. 6 is a graph illustrating the roles of agglomerate density and diameter in the time to deposit 90% of suspended ENM. Density and particle size both play important roles in determining the rate of ENM deposition. The combined effects of these two parameters results in a wide range, among the ENMs investigated, in the rate of deposition and consequently the time required for 90% of the ENM in suspension to be deposited, indicated here by $T_{90}$. Effective density ($\rho_{EV}$) is represented along the x axis. The diameter of the bubbles corresponding to each ENM represents and is relatively scaled to the agglomerate or hydrodynamic diameter ($d_H$) of the ENM. The primary particle diameter ($d_{BET}$) is indicated, along with $d_H$, for each ENM in the text corresponding to its bubble in the graph.

PCV tubes, originally designed and typically used for measuring biomass of suspension cultures of mammalian cells (Stettler et al., 2006, Biotechnol. Bioeng. 95(6):1228-1233), consist of an upper chamber for sample loading, which tapers to a lower 5 μl, 500 μm diameter volumetric pellet-capturing capillary (FIG. 4C). One ml of ENM suspensions, prepared as described in detail below (50, 100 or 250 μg/mL), were loaded into PCV tubes and centrifuged at an optimized high speed (described elsewhere herein; 1,000, 2,000 or 3,000×g), for one hour. Agglomerate pellet volumes were measured using a simple slide rule-like device available from the PCV tube manufacturer. Agglomerate densities were then calculated from pellet volumes based on the rationale and equations derived as follows:

The effective density of an ENM agglomerate in a liquid suspension, $\rho_E$, is defined as:

$$\rho_E = \frac{M_{agg}}{V_{agg}}, \quad (3)$$

where $M_{agg}$ and $V_{agg}$ are the ENM agglomerate mass and volume, respectively. Since agglomerates are composed of ENM particles and media trapped between and among the ENM particles (intra-agglomerate media), the mass of an agglomerate can be expressed as:

$$M_{agg} = M_{media} + M_{ENM}, \quad (4)$$

where $M_{media}$ and $M_{ENM}$ are the masses of intra-agglomerate media and ENM respectively (FIGS. 4A-4C).

Expressing density in terms of mass and volume, and substituting into equation 4 yields:

$$\rho_E = \frac{(\rho_{media} V_{media}) + (\rho_{ENM} V_{ENM})}{V_{agg}}, \quad (5)$$

where $\rho_{media}$ and $\rho_{ENM}$ are the known densities (g/cm³) of the media and ENM, respectively, and $V_{media}$ and $V_{ENM}$ are the volumes of the media and ENM, respectively. Media densities were calculated from the mass of a 50 mL sample by subtracting the weight of a 50 mL volumetric flask from the weight of the same flask containing 50 mL (TC) of media.

Following centrifugation of an ENM suspension in PCV tubes, the pellet collected in the volumetric capillary consisted of stacked ENM agglomerates, along with additional inter-agglomerate media interspersed between the formed agglomerates, and distinct from intra-agglomerate media trapped within agglomerates (FIGS. 4A-4C). From the volume of the pellet, $V_{pellet}$ (cm³), which is directly measured using the PCV method described elsewhere herein, $V_{agg}$ can be estimated as $$V_{agg} = V_{pellet} \times SF \quad (6)$$

where the inter-agglomerate media is accommodated by a stacking factor, SF (volume/volume, unitless), which denotes the fractional contribution of ENM agglomerates to the pellet, and which depends on agglomerate shape and deformability. In the case of perfect hard spheres, possible values for SF may range from 0.634—the maximum SF for random dense stacking of hard spheres (Song et al., 2008, Nature 453(7195):629-632)—to the theoretical maximum for regularly stacked hard spheres, 0.74048 (Gauss, 1831, Göttingsche Gelehrte Anzeigen 2:9). SF can possibly range to higher values, given that agglomerates may deform within the pellet formed under a high centrifugal field (e.g., 2000×g) to minimize inter-agglomerate space. Directly measuring the inter-agglomerate media volume between the stacked pellet agglomerates is a challenge and no known method has been reported for directly measuring SF.

In the present study, for comparison purposes, stacking factors of 0.74048 (regular dense spherical stacking), and 0.637 (a value previously reported in the literature as an estimate for the intra-agglomerate packing factor; Sterling et al., 2005, Water Res. 39(9):1818-3034) were used in the calculations of effective density. A method for estimating values for SF for fractal chain-like agglomerates based on empirical measurement of ENM behavior in liquid suspension by analytical ultracentrifugation is proposed elsewhere herein.

Since the agglomerates consist of ENM and intra-agglomerate media, $V_{media}$ can be calculated from $V_{agg}$ as $$V_{media} = V_{agg} - V_{ENM} \quad (7)$$

The volume of ENM in the pellet, $V_{ENM}$ (cm³), can be calculated from the ENM density and the mass of ENM dissolved or remaining suspended in the supernatant, $M_{ENMsn}$, can be calculated as follows $$V_{ENM} = \frac{M_{ENM} - M_{ENMsn}}{\rho_{ENM}}. \quad (8)$$

$M_{ENMsn}$ can be directly measured by inductively coupled plasma mass spectrometry (ICP-MS) analysis of supernatants, described in further detail elsewhere herein. Its effect on the estimation of effective density was evaluated in this study.

Finally, the effective agglomerate density, $\rho_E$, is thus calculated by substituting the expressions for $V_{agg}$, $V_{media}$, and $V_{ENM}$ from Equations 6, 7 and 8, respectively, into Equation 5, as follows:

$$\rho_E = \frac{\rho_{media}\left(V_{pellet} SF - \frac{M_{ENM} - M_{ENMsn}}{\rho_{ENM}}\right) + \rho_{ENM}\left(\frac{M_{ENM} - M_{ENMsn}}{\rho_{ENM}}\right)}{V_{pellet} SF}, \quad (9)$$

which can be simplified and rewritten as $$\rho_E = \frac{\rho_{media} V_{pellet} SF + \left[\left(1 - \frac{\rho_{media}}{\rho_{ENM}}\right) \times (M_{ENM} - M_{ENMsn})\right]}{V_{pellet} SF}. \quad (10)$$

Finally, upon measuring $M_{ENMsn}$ by ICP-MS, if it is determined that $M_{ENMsn} \ll M_{ENM}$, we can assume the contribution of $M_{ENMsn}$ to be negligible, and simplify Equation 10 as:

$$\rho_E = \rho_{media} + \left[\left(\frac{M_{ENM}}{V_{pellet} SF}\right)\left(1 - \frac{\rho_{media}}{\rho_{ENM}}\right)\right]. \quad (11)$$

Stacking Factor Determination by Analytical Ultracentrifugation

Analytical ultracentrifugation (AUC) has been used in the investigation of physical properties (e.g., size or shape) and interactions of proteins and biomolecules (Howlett et al., 2006, Curr. Opin. Chem. Biol. 10(5):430-6). Recently, AUC has also been employed for the characterization of nanomaterials (Jamison et al., 2008, ACS Nano 2(2):311-9; Arnold et al., 2008, ACS Nano 2(11):291-300).

From the sedimentation velocity of ENMs in liquid suspension measured by AUC, the density of the agglomerate can be expressed, replacing the gravitational field, g, with the centrifugal field, and rearranging, as $$\rho_{agg} = \frac{18\mu v}{\omega^2 r d^2} + \rho_{media}, \quad (12)$$

where ω is the angular velocity (rad/s) and r is the distance from the center of rotation (m) at which the velocity was measured. The stacking factor can then be determined by equating $\rho_E$ in Equation 11, and $\rho_{agg}$ in equation 12, and solving for SF, to yield $$SF = \frac{\omega^2 r d^2 \left[\left(1 - \frac{\rho_{media}}{\rho_{ENM}}\right) \times (M_{ENM} - M_{ENMsn})\right]}{18\mu v V_{pellet}}, \text{ or} \quad (13)$$

$$SF = \frac{d^2 M_{ENM}}{18\eta s V_{pellet}} \cdot \left[\left(1 - \frac{\rho_{media}}{\rho_{ENM}}\right)\right]$$

The SF for ENMs of variable material density and morphology dispersed in cell culture media was determined using a Beckman-AUC Coulter XL-1 (Brea, Calif.). Dispersions of VENGES SiO$_2$ (d$_{BET}$=18.6 nm), VENGES CeO$_2$ (d$_{BET}$=5.4 nm), and gold nanospheres (d$_H$=42.2 nm) were prepared in RPMI/10% FBS at a concentration of 0.1 mg/ml. Approximately 400 µl of each dispersion were centrifuged up to 250,000×g at 20° C., using a ProteomeLab™ XL-A/XL-I An-60 Ti rotor (Beckman Coulter, Brea, Calif., USA) equipped with interference optics. Reference cells were filled with equivalent volumes of ENM-free RPMI/10% FBS. Raw data collected from AUC measurements were used to calculate sedimentation velocities for each ENM using the analysis software Sedfit (Zook et al., 2011, ACS Nano 5(10):8070-9; Schuck, 2000, Biophys. J. 78(3):1606-19). SF was then calculated for these materials using Equation 13.

Estimation of Effective Density—Sterling Method

For comparison purposes, effective densities were also calculated for all ENMs based on the Sterling model (Hinderliter et al., 2010, Part. Fibre Toxicol. 7(1):36; Sterling et al., 2005, Water Res. 39(9):1818-30), assuming a specific fractal dimension (DF) of 2.3 and a packing factor (PF) of 0.637. The number of single particles per agglomerate (Np), agglomerate porosity ($\epsilon_a$, unitless), and effective density ($\rho e$, g/cm$^3$) were subsequently calculated from the hydrodynamic diameter of the agglomerate measured by DLS (d$_H$, nm), primary particle diameter (d$_{BET}$, nm), primary particle density ($\rho_p$, g/cm$^3$), media density ($\rho_{media}$, g/cm$^3$), fractal dimension (DF), and packing factor (PF) as previously described (Cohen et al., 2012, Nanotoxicol. doi:10.3109/17435390.2012.666576; Hinderliter et al., 2010, Part. Fibre Toxicol. 7(1):3630; Sterling et al., 2005, Water Res. 39(9):1818-30) (equations 8-10).

Optimization of Centrifugation Protocol

To optimize the centrifugation protocol and ensure that all or most of the ENMs in solution suspension were collected in the pellet, dispersions of CeO$_2$ (d$_{BET}$=5.4 nm) suspended in RPMI/10% FBS were centrifuged at 1000, 2000, or 3000×g for 1 hour. Following centrifugation, samples collected from the supernatants were analyzed by DLS and by inductively coupled mass spectrometry (IC-PMS) to determine the amount of ENM remaining in the supernatant after centrifugation (FIGS. 4A-4C).

Optimization of ENM Concentration

Dispersions of CeO$_2$ (d$_{BET}$=5.4 nm) were prepared in RPMI/10% FBS over a range of various mass/volume concentrations commonly used for in vitro toxicological assays (50 µg/mL, 100 µg/mL, or 250 µg/mL), centrifuged at 2,000×g for 1 hour, and evaluated for effective density in order to assess the effect of ENM concentration on its measurement.

Impact of Dispersion Media on Effective Density

Considering the substantial effects that media characteristics (such as pH, conductance, and protein content) have on ENM interactions in liquid suspension (Cohen et al., 2012, Nanotoxicol. doi:10.3109/17435390.2012.666576; Taurozzi et al., 2010, Nanotoxicol. doi:10.3109/17435390.2012.665506), we examined the effect of media composition on ENM effective density. The effective density protocol described herein was applied to dispersions of CeO$_2$ (d$_{BET}$=5.4 nm) suspended in four different media commonly used for in vitro toxicity studies (RPMI alone, RPMI/10% FBS, F12K alone, and F12K/10% FBS).

Dosimetric Considerations

The in vitro sedimentation, diffusion and dosimetry (ISDD) model proposed by Hinderliter and co-workers (Hinderliter et al., 2010, Part. Fibre Toxicol. 7(1):36) was used to calculate numerically, for each ENM dispersion, the fraction of administered particles that would be deposited onto cells in a standard 96-well plate as a function of time f$_D$(t).

The ISDD model is based on a parabolic partial differential equation:

$$\frac{\partial n}{\partial t} = D\frac{\partial^2 n}{\partial x^2} - V\frac{\partial n}{\partial x} \quad (14)$$

where t is time (s), x is distance (m), D is the diffusion coefficient (m$^2$/s), as defined in equation 1, V is the sedimentation velocity (m/s), as defined in equation 2, and n is the particle concentration (g/cm$^3$). The model assumes a uniform particle distribution at the initiation of the experiment, and includes the following boundaries: no particle flux across the top of the media, and zero concentration at the bottom.

The particle hydrodynamic diameter, d$_H$, as measured by DLS, and the measured effective density were used as input to the model. Additionally, the following parameters were used as input to the ISDD numerical model: media column height, 3.15 mm; temperature, 310K; media density, 1.00 g/ml; viscosity, 0.00074 Pa·s (Hinderliter et al., 2010, Part. Fibre Toxicol. 7(1):36); and administered (initial suspension) particle concentration, 100 µg/ml.

For each ENM dispersion, the model-derived f$_D$(t) was fit to a Gompertz sigmoidal equation in order to determine the particle/media-specific deposition fraction constant, which was in turn used to calculate the time required for delivery of 90% of the administered dose, t$_{90}$, for each ENM dispersion using the specific deposition function constants, α, and an f$_D$(t) value of 0.90 (Cohen, J., et al., 2012, Nanotoxicol. doi:10.3109/17435390.2012.666576; equations 11-12).

ICP-MS Analysis

All ICP-MS sample preparation was conducted in a Class 100 trace metal free clean hood in the Earth and Ocean Sciences Department at Duke University. Before preparation, samples were agitated with a GlobalSpec (Troy, N.Y. USA) Laboratory shaker for 30 minutes, followed by 1 minute of vortex shaking to ensure re-homogenization of the fluid.

Class A polypropylene test tubes were pre-washed using a 5% nitric acid bath to remove potential metal contamination. Approximately 0.1 mL of each sample was volumetrically pipetted into the corresponding pre-labeled analytical vials and verified gravimetrically to ±0.001 mg. Dilutions were prepared volumetrically (and validated gravimetrically) by adding water purified to 18.2 MΩcm resistance (Milli-Q water purification system, Millipore, Bedford, Mass., USA) to achieve sample dilution of ~100× and then acidified using trace metal free concentrated (15.9 mol L$^{-1}$) ultra-pure nitric acid (HNO$_3$) (Fisher Scientific, MA, USA). Internal standards consisting of known quantities of indium (In) and bismuth (Bi) were added to the samples to correct for instrumental drift. Sample dilution resulted in a final concentration of 2% HNO$_3$ (by volume), and 10 ng/g and 1 ng/g of the internal standards, respectively. All analytical standards, procedural blanks, and interference check standards were prepared in an analogous fashion.

Cerium content was measured using a Perkin Elmer Axiel Field Technology DRC II inductively coupled plasma mass spectrometer (ICP-MS). Prior to sample analysis, the ICP-MS was optimized for sensitivity, stability, and to reduce the formation of doubly charged species and oxide interferences using a multi-element tuning solution containing Mg, In, Ba, Ce, Bi, and U. Optimization continued until CeO$^+$/Ce$^+$ and Ba$^{++}$/Ba$^+$ was simultaneously less than 2%. These interferences were quantified to correct for instrumental and procedural backgrounds and isobaric interferences, respectively. During sample analysis sample lines were rinsed to reduce memory effects by washing sequentially with water purified to 18.2 MΩcm resistance (Milli-Q water purification system, Millipore, Bedford, Mass., USA) for 120 seconds and a 2% $HNO_3$ solution for an additional 120 seconds between analyses.

ICP-MS analyses were conducted according to previously reported methods (Darrah, 2009, Metallomics 1:9; McLaughlin et al., 2011, Inorg. Chem. 50:2). Throughout the analysis, the $CeO^+/Ce^+$ remained <2.1%. Ce detection was performed by simultaneously monitoring $^{140}Ce$ and $^{142}Ce$. No isobaric interferences were observed for $^{140}Ce$ and $^{142}Ce$ was corrected for Ne interferences. Calculated solution concentrations obtained from $^{140}Ce$ and $^{142}Ce$ varied by less than 3.1% on average. [Ce] quantification was obtained using a 7-point external calibration curve spiked with known quantities of Ce in a linear range from 0.050 ng/g to 100 ng/g (McLaughlin et al., 2011, Inorg. Chem. 50(22):11294-11296; Darrah et al., 2009, Metallomics 1(6):479-488). Known aliquots of Ce spikes were analyzed as unknowns to determine external precision as 2.7%. Five duplicate analyses (n=5) were performed for all analytes for each sample solution.

Example 1

Characterization of ENM Powders

Properties of ENM powders, including specific surface area (SSA), $d_{BET}$, and $d_{XRD}$, are summarized in Table 1.

Representative TEM/SEM of the nanomaterials studied are illustrated in FIGS. 3A-3F. Metal oxide ENMs demonstrated the chain-like aggregates typical of these materials, whereas individual spherical particles were clearly seen in the SEM/TEM images of gold nanospheres, which are an example of an ENM of known regular shape that is highly monodispersed when suspended in water (FIGS. 3A-3F).

TABLE 1

ENM powder properties

| Material | SSA ($m^2/g$) | $d_{BET}$ (nm) | $d_{XRD}$ (nm) | $\rho_p$ ($g/cm^3$) |
|---|---|---|---|---|
| VENGES $SiO_2$ | 147 | 18.6 | NA | 2.648 |
| VENGES $Fe_2O_3$ | 41.5 | 27.6 | 19.6 | 5.242 |
| VENGES $CeO_2$ | 144 | 5.4 | 9.5 | 7.215 |
| VENGES $CeO_2$ | 59 | 13.3 | 23.7 | 7.215 |
| VENGES $CeO_2$ | 11 | 71.3 | 119 | 7.215 |
| EVONIK $SiO_2$ | 200 | 14 | N/A | 2.648 |
| EVONIK $TiO_2$ | 50 | 21 | 33 | 4.23 |
| Sigma Aldrich CuO | 17.23 | 58.0 | 22 | 6.315 |
| Alfa Aesar ZnO | 17 | 63 | 22.3 | 5.606 |
| gold nanospheres | NA* | 20* | 20* | 19.3 |

NA*: not applicable as material was generated in wet suspension; the primary particle size here was estimated from TEM images of nanospheres in suspension.
SSA: specific surface area by nitrogen adsorption/Brunauer-Emmett-Teller (BET) method.
$d_{BET}$: particle diameter determined from SSA and material density, $\rho_p$, as described elsewhere herein.
$d_{XRD}$: particle diameter by X-ray diffraction.

TABLE 2

Properties of ENM dispersions in RPMI/10%FBS

| Material | $d_{BET}$ (nm) | $d_H$ (nm) | PdI | ζ(mV) | σ (mS/cm) | pH |
|---|---|---|---|---|---|---|
| VENGES $SiO_2$ | 18.6 | 135.5 ± 9.53 | 0.715 ± 0.055 | −10.8 ± 1.57 | 14.1 ± 0.737 | 7.22 ± 0.074 |
| VENGES $Fe_2O_3$ | 27.6 | 380 ± 3.60 | 0.151 ± 0.070 | −12.2 ± 0.929 | 12.2 ± 0.751 | 7.74 ± 0.086 |
| VENGES $CeO_2$ | 5.4 | 179 ± 3.76 | 0.294 ± 0.022 | −14.3 ± 0.751 | 10.4 ± 0.1 | 8.16 ± 0.062 |
| VENGES $CeO_2$ | 13.3 | 181 ± 29.8 | 0.120 ± 0.095 | −12.0 ± 0.329 | 11.9 ± 0.0883 | 8.19 ± 0.073 |
| VENGES $CeO_2$ | 71.3 | 131 ± 5.17 | 0.171 ± 0.021 | −9.77 ± 0.497 | 11 ± 0.152 | 7.95 ± 0.05 |
| EVONIK $SiO_2$ | 14 | 147 ± 3.04 | 0.031 ± 0.022 | −12.2 ± 0.25 | 11.3 ± 0.17 | 8.43 ± 0.081 |
| EVONIK $TiO_2$ | 21 | 457 ± 20.9 | 0.177 ± 0 | −10.9 ± 0.55 | 10.5 ± 0.42 | 8.45 ± 0.11 |
| Sigma Aldrich CuO | 58.0 | 310 ± 7.57 | 0.269 ± 0.024 | −9.43 ± 0.497 | 11.6 ± 0.493 | 7.85 ± 0.08 |
| Alfa Aesar ZnO | 63 | 307 ± 96.5 | 0.303 ± 0.122 | −8.94 ± 1.22 | 12.5 ± 1.82 | 7.74 ± 0.11 |
| gold nanospheres | NA* | 42.2 ± 24.7 | 0.403 ± 0.207 | −9.29 ± 2.0 | 12.0 ± 1.14 | 7.70 ± 0.13 |

| Material | $\rho_{ENM}$ ($g/cm^3$) | SF | $\rho_{EV}$ ($g/cm^3$) | $\rho_{ES}$ ($g/cm^3$) |
|---|---|---|---|---|
| VENGES $SiO_2$ | 2.648 | 0.538 | 1.131 ± 0.001 | 1.410 |
| VENGES $Fe_2O_3$ | 5.242 | 0.634 | 1.518 ± 0.03 | 1.516 |
| VENGES $CeO_2$ | 7.215 | 0.610 | 1.492 ± 0.007 | 1.536 |
| VENGES $CeO_2$ | 7.215 | 0.610 | 1.650 ± 0.008 | 1.999 |
| VENGES $CeO_2$ | 7.215 | 0.610 | 2.421 ± 0.041 | 5.060 |
| EVONIK $SiO_2$ | 2.648 | 0.538 | 1.171 ± 0.003 | 1.318 |

TABLE 2-continued

| | | | | |
|---|---|---|---|---|
| EVONIK TiO$_2$ | 4.23 | 0.634 | 1.315 ± 0.007 | 1.374 |
| Sigma Aldrich CuO | 6.315 | 0.634 | 2.099 ± 0.031 | 2.644 |
| Alfa Aesar ZnO | 5.606 | 0.634 | 1.650 ± 0.07 | 2.520 |
| gold nanospheres | 19.3 | 0.764 | 17.18 ± 0.35 | 15.07 |

$d_H$: hydrodynamic diameter,
PdI: polydispersity index,
ζ: zeta potential,
σ: specific conductance
$d_H$: hydrodynamic diameter determined by DLS,
$\rho_{ENM}$: raw ENM material density,
SF: stacking factor,
$\rho_{EV}$: effective density estimated by volumetric centrifugation,
$\rho_{ES}$: effective density estimated by Sterling equation.

Example 2

ENM Dispersal and Characterization in Liquid Suspensions

Properties of ENM dispersions in RPMI/10% FBS measured by DLS are summarized in Table 2. Agglomerate sizes of the metal oxide particles were typically on the order of 130 nm or larger, with low polydispersity (PdI<0.3). In contrast, gold nanospheres exhibited an average hydrodynamic diameter of 44 nm. Relatively high polydispersity values were observed for SiO$_2$ and the gold nanospheres, which is likely attributable to detection of free proteins present in the media that were not bound on the particle surface.

Example 3

Experimental Determination of Effective Density

Stacking Factor (SF) Determination by Analytical Ultracentrifugation (AUC)

The sedimentation velocities for VENGES SiO$_2$ ($d_{BET}$=18.6 nm), VENGES CeO$_2$ ($d_{BET}$=13.3 nm), and gold nanospheres ($d_H$=42.2 nm) dispersed in RPMI/10% FBS were determined by AUC, and ENM-specific values for SF were calculated using Equation 13.

The VENGES generated ENMs exhibiting chain-like fractal morphology exhibited similar values for SF, around 0.5. Specifically, stacking factors for the CeO$_2$, and SiO$_2$ were estimated from AUC sedimentation coefficient profiles as 0.610 and 0.538, which are close to the theoretical value of 0.634 given their spherical agglomerate shape for random packing of uniform spheres.

The SF calculated for gold nanospheres (0.764) was consistent with estimates from the literature for packing of perfect spheres (SF=0.7408; Gauss, 1831, Göttingsche Gelehrte Anzeigen 2:9). The rough estimate for SF of 0.5, as determined by AUC, was assumed to be generalizable for the class of flame generated metal oxide ENMs exhibiting similar fractal morphology.

It should be pointed out that due to minor differences in polydispersity or agglomerate shape, SF values may not be exactly identical among ENMs of a given class, as observed for CeO$_2$ (SF=0.610) and SiO$_2$ (SF=0.538). However, both of these observed values are close to the theoretical value of 0.634, and the corresponding change in ρEV resulting from a small change in SF was relatively small. For example, replacing the estimated SF for CeO$_2$ with a 50% larger value (0.910) results in only an 11% change in calculated $\rho_{EV}$ (from 1.492 to 1.333 mg/cm$_3$). Moreover, given the morphological similarity among ENMs of the flame-generated metal oxide class, differences in SF within this class may generally be acceptably small, as it should likewise be within other classes of ENMs.

Optimization of Centrifugation Protocol

As summarized in Table 3, ICP-MS analysis for CeO$_2$ ($d_{BET}$=5.4 nm) revealed negligible amounts of unpelleted ENM in supernatants ($M_{ENMsn}$<4% of total ENM suspended) at all centrifugation speeds, with an effect on effective density of less than 2%. Based on these results, in all subsequent calculations, $M_{ENM}$ was assumed to be negligible and omitted from the calculations of effective density.

Negligible differences were observed between the effective densities calculated for dispersions centrifuged at 1,000× g, 2,000×g, or 3,000×g for 1 hour, presented in Table 3A (1.342 g/cm$^3$, 1.303 g/cm$^3$, and 1.321 g/cm$^3$ for 1,000×g, 2,000×g, and 3,000×g respectively). Based on these results, in all subsequent experiments ENM suspensions were centrifuged for 1 hour at 2,000×g (optimum centrifugation conditions).

Although forces exerted on ENMs during low speed centrifugation are very small, in order to rule out the possibility that agglomerate structures were altered by centrifugation we performed atomic force microscopy (AFM) experiments. Forces up to six orders of magnitude greater than those experienced during centrifugation were applied to agglomerates deposited onto a sample grid either prior to or following centrifugation, and deformation of agglomerates was assessed. The results of these experiments revealed that forces experienced by agglomerates during low speed centrifugation do not result in their deformation, suggesting that agglomerates most likely maintained their original architecture during the low speed centrifugation employed during the experiments.

Tables 3A-3C: Optimization of Effective Density Measurement Protocol

TABLE 3A

CeO$_2$ ($d_{BET}$ = 5.4 nm) dispersed at 100 μg/ml in RPMI/10% FBS, and centrifuged at various speeds for 1 hour: material density ($\rho_p$); measured effective density ($\rho_E$ ± S.D.); percent mass remaining in supernatant (% $M_{ENMsn}$); effective density corrected for ENM remaining in supernatant ($\rho^*_E$ ± S.D.)

| Speed (×g) | $\rho_P$ (g/cm$^3$) | $\rho_E$ (g/cm$^3$) | % $M_{ENMsn}$ | $\rho^*_E$ (g/cm$^3$) |
|---|---|---|---|---|
| 1000 | 7.215 | 1.342 ± 0.006 | 3.35 ± 0.037 | 1.319 ± 0.003 |
| 2000 | 7.215 | 1.303 ± 0.004 | 1.68 ± 0.076 | 1.299 ± 0.004 |
| 3000 | 7.215 | 1.321 ± 0.003 | 0.763 ± 0.012 | 1.330 ± 0.005 |

TABLE 3B

CeO$_2$ (d$_{BET}$ = 5.4 nm) dispersed at various concentrations in RPMI/10% FBS, and centrifuged at 2000 × g for 1 hour: material density ($\rho_p$); measured effective density ($\rho_E$ ± S.D.)

| Concentration (μg/ml) | $\rho_P$ (g/cm$^3$) | $\rho_E$ (g/cm$^3$) |
|---|---|---|
| 50 | 7.215 | 1.235 ± 0.000 |
| 100 | 7.215 | 1.303 ± 0.004 |
| 250 | 7.215 | 1.298 ± 0.003 |

TABLE 3C

CeO$_2$ (d$_{BET}$ = 5.4 nm) dispersed at 100 μg/ml in RPMI/10% FBS, and centrifuged at 2000 × g for 1 hour: media density ($\rho_{media}$); material density ($\rho_p$); measured effective density ($\rho_E$ ± S.D.). Differences may be linked to dependence of agglomerate structure on media-particle specific properties.

| Media | $\rho_{media}$ (g/cm$^3$) | $\rho_P$ (g/cm$^3$) | $\rho_E$ (g/cm$^3$) |
|---|---|---|---|
| RPMI/10% FBS | 1.0084 | 7.215 | 1.303 ± 0.004 |
| RPMI | 1.0072 | 7.215 | 1.233 ± 0.002 |
| F12K | 1.007 | 7.215 | 1.193 ± 0.011 |
| F12K/10% FBS | 1.0084 | 7.215 | 1.240 ± 0.007 | shown in Table 3B. These data reveal only small differences (<5%) between effective densities measured at different concentrations (1.235 g/cm$^3$, 1.303 g/cm$^3$, and 1.298 g/cm$^3$ at 50 μg/mL, 100 μg/mL, and 250 μg/mL, respectively), and demonstrate that the present method for estimating effective density is relatively independent of ENM concentration, and generates consistent results at concentrations commonly used for in vitro toxicity assays.

Example 5

Impact of Dispersion Media on Effective Density

Table 3C presents results for CeO$_2$ (d$_{BET}$=5.4 nm) dispersed in various media commonly used for in vitro toxicity studies (RPMI, RPMI/10% FBS, F12K, F12K/10% FBS). Not surprisingly, small differences were observed between effective densities measured in the different media formulations (1.233 g/cm$^3$, 1.303 g/cm$^3$, 1.193 g/cm$^3$, and 1.240 g/cm$^3$ for RPMI, RPMI/10% FBS, F12K, and F12K/10% FBS respectively).

Example 6

Effective Density Measurements for ENM Panel

Effective densities for all ENMs in the panel (dispersed at 100 μg/ml in RPMI/10% FBS and centrifuged at 2,000×g for 1 hour) are summarized in Table 4.

TABLE 4

Comparison of the material density ($\rho_p$), Sterling equation-estimated effective density ($\rho_{ES}$), PCV centrifugation-measured effective density with a packing factor (SF) = 1.0 ($\rho_E$), measured effective density with SF = 0.74048 ($\rho_E$'), and measured effective density with SF = 0.637 ($\rho_E$''). ENMs dispersed in RPMI/10%FBS and centrifuged at 2000 × g for one hour.

| Material | d$_{BET}$ (nm) | $\rho_P$ (g/cm$^3$) | $\rho_{ES}$ (g/cm$^3$) | $\rho_E$ (g/cm$^3$) | $\rho_E$'(g/cm$^3$) | $\rho_E$''(g/cm$^3$) |
|---|---|---|---|---|---|---|
| VENGES SiO$_2$ | 18.6 | 2.648 | 1.410 | 1.074 ± 0.001 | 1.097 ± 0.001 | 1.112 ± 0.001 |
| VENGES Fe$_2$O$_3$ | 27.6 | 5.242 | 1.516 | 1.332 ± 0.019 | 1.445 ± 0.026 | 1.516 ± 0.030 |
| VENGES CeO$_2$ | 5.4 | 7.215 | 1.536 | 1.303 ± 0.004 | 1.407 ± 0.006 | 1.472 ± 0.007 |
| VENGES CeO$_2$ | 13.3 | 7.215 | 1.999 | 1.400 ± 0.005 | 1.537 ± 0.007 | 1.622 ± 0.008 |
| VENGES CeO$_2$ | 71.3 | 7.215 | 5.060 | 1.870 ± 0.025 | 2.172 ± 0.034 | 2.361 ± 0.039 |
| EVONIK SiO$_2$ | 14 | 2.648 | 1.318 | 1.096 ± 0.002 | 1.127 ± 0.002 | 1.146 ± 0.003 |
| EVONIK TiO$_2$ | 21 | 4.23 | 1.374 | 1.203 ± 0.004 | 1.271 ± 0.006 | 1.314 ± 0.007 |
| Sigma Aldrich CuO | 58.0 | 6.315 | 2.644 | 1.700 ± 0.020 | 1.943 ± 0.026 | 2.094 ± 0.031 |
| Alfa Aesar ZnO | 63 | 5.606 | 2.520 | 1.415 ± 0.045 | 1.558 ± 0.060 | 1.647 ± 0.070 |
| Gold Nanospheres | NA* | 19.3 | 15.074 | 13.38 ± 0.26 | 17.72 ± 0.36 | 20.43 ± 0.41 |

Example 4

Impact of ENM Concentration on Effective Density

In order to determine the effect of ENM concentration on effective density measurements, dispersions of CeO$_2$ (d$_{BET}$=5.4 nm) were prepared in RPMI/10% FBS over a range of various mass/volume concentrations commonly used for in vitro toxicological assays (50 μg/mL, 100 μg/mL, or 250 μg/mL), centrifuged at 2,000×g for 1 hour, and evaluated for effective density. The effective densities calculated for CeO$_2$ (d$_{BET}$=5.4 nm) at 50 μg/mL, 100 μg/mL and 250 μg/mL are Effective densities are shown here over a range of stacking factors (SF), corresponding to (i) ideal stacking with no space between agglomerates (SF=1.0), (ii) perfectly ordered dense stacking of hard spheres (SF=0.74048; Gauss, 1831, Göttingsche Gelehrte Anzeigen 2:9), and (iii) a value previously reported in the literature to estimate intra-agglomerate packing (SF=0.637; Sterling et al., 2005, Water Res. 39(9):1818-30), the latter value being also very close to the theoretical value for maximally efficient random packing of hard spheres (0.634; Song et al., 2008, Nature 453(7195):629-32).

Ideal stacking (SF=1.0) would require that agglomerates (or spheres in the case of the gold nanospheres in the panel)

within the pellet be arranged with no intervening space; considering that agglomerate surfaces are highly irregular (and that our gold particles are hard spheres), this degree of stacking may be unlikely. The value corresponding to intra-agglomerate packing (SF=0.637) reflects packing of irregularly shaped particles in the absence of compression forces. Since the pellets are actually formed under great compression force, somewhat greater stacking efficiency may be observed. The correct stacking factor may thus lie somewhere between these two extremes, and that the effective densities in Table 4 calculated with SF=0.74048 are likely the most accurate, with those calculated at the higher and lower SF values being somewhat lower and somewhat greater, respectively. In Equation 10, as the density of the ENM increases, the second term in the numerator approaches zero, thereby increasing the effect of SF on effective density. Not surprisingly, therefore, the effect of SF is seen in Table 4 to be relatively small for lighter ENMs (for VENGES $SiO_2$, $\rho_{E'}$ at SF=0.637 is 1.3% greater than $\rho_{E''}$ at SF=0.74048), and maximal in the case of gold nanospheres ($\rho_{E'}$ at SF=0.637 is 20% greater than $\rho_{E''}$ at SF=0.74048). Accordingly, in the following discussion, unless otherwise specified, effective densities were calculated with the assumption of tight, ordered spherical stacking, with SF=0.74048.

Small differences in effective densities were observed between metal oxide ENMs, most of which exhibited effective densities close to that of the dispersion media RPMI/10% FBS, 1.0084 g/cm$^3$ (Tables 2 and 3). Effective density generally correlated with raw material density. The lowest effective density was observed for VENGES $SiO_2$ (1.097 g/cm$^3$ at SF=0.74047, $\rho_{E'}$ in Table 4), and was close that observed for the commercially purchased EVONIK $SiO_2$ (1.127 g/cm$^3$), consistent with the low density of $SiO_2$ (2.648 g/cm$^3$). In contrast, gold nanospheres and $CeO_2$ ($d_{BET}$=71.3 nm) exhibited the highest effective densities (17.72 g/cm$^3$ and 2.172 g/cm$^3$ respectively) corresponding to the highest material densities (19.3 g/cm$^3$ and 7.215 g/cm$^3$ respectively). In the case of gold nanospheres, the high effective density is likely a result of the lack of a chain like fractal geometry, and absence of agglomeration, thereby enabling highly efficient stacking of particles. TEM images confirmed that the monodisperse and spherical morphology of these particles is distinct from the fractal and irregular chain-like agglomerates characteristic of metal oxides generated by flame spray pyrolysis (FIGS. 3A-3F). The small difference between material and effective density of the gold nanospheres (19.3 g/cm$^3$ vs. 17.72 g/cm$^3$ at SF=0.74048) may reflect small amounts of media and protein coating the particles when dispersed in RPMI/10% FBS. In general, effective density correlated with material density (gold nanospheres>$CeO_2$>CuO>ZnO>$Fe_2O_3$>$TiO_2$>$SiO_2$). Effective density also appeared to correlate with primary particle size for various $CeO_2$ ENMs investigated ($\rho_E$ of 2.172 g/cm$^3$, 1.537 g/cm$^3$, and 1.407 g/cm$^3$ at SF=0.74048 for $CeO_2$ with $d_{BET}$ of 71.3 nm, 13.3 nm, and 5.4 nm, respectively).

Table 4 also includes effective densities ($\rho_e$, g/cm$^3$) estimated using the Sterling method, using best-guess values for fractal dimension of 2.3 and packing factor of 0.637, for comparison alongside the measured effective density values. Compared with the present measurements, estimates based on the Sterling model consistently overestimated effective density. This is especially evident for $CeO_2$ ($d_{BET}$=71.3 nm) where the Sterling-estimated density was greater than the presently estimated density by a factor of 2.4 ($\rho_{ES}$=5.060 g/cm$^3$; $\rho_{E'}$=2.172 g/cm$^3$ at SF=0.74048), and for ZnO, for which the Sterling-estimated density was greater than our estimated density by a factor of 1.6 ($\rho_e$=2.520 g/cm$^3$; $\rho_{ES}$=1.558 g/cm$^3$ at SF=0.74048). These differences were likely due to material-specific packing inefficiencies, not accounted for by the best guess packing factor and fractal dimension values used in the Sterling equation.

Effective densities for all ENMs were further determined using equation (11). For $CeO_2$, $SiO_2$ and Au spheres, the SF values used to calculate $\rho_{EV}$ were those determined from equation (13). The theoretical SF value for randomly packed spheres (0.634) was used to calculate $\rho_{EV}$ for all other metal oxide ENMs (Table 2). Whereas gold nanospheres exhibited a $\rho_{EV}$ value only slightly less than the density of elemental gold (17.18 vs. 19.3 mg/cm$^3$), consistent with minimal agglomeration, all other ENMs exhibited $\rho_{EV}$ values closer to the density of the dispersion media (RPMI/10% FBS, 1.0084 g/cm$^3$) than to that of the raw ENM. In one embodiment, this indicates that in this particular fluid these ENMs formed agglomerates containing large amounts of trapped intra-agglomerate media (FIGS. 4A-4C). It is worth noting that since ENMs that form agglomerates possess $\rho_{EV}$ values closer to the dispersion media density, $\rho_{EV}$ represents an indirect indicator of agglomeration state for ENMs in suspension. In general $\rho_{EV}$ for flame-generated metal oxide ENMs correlated with raw material density, which may suggest that agglomerates of these ENMs are composed of comparable relative proportions of raw ENM and trapped media. Effective density also correlated with primary particle size among the three $CeO_2$ ENMs investigated ($\rho_{EV}$ of 2.421, 1.650, and 1.492 g/cm$^3$ for $CeO_2$ with $d_{BET}$ of 71.3, 13.3, and 5.4 nm, respectively). For many of the ENMs investigated $\rho_{EV}$ and $\rho_{ES}$ (estimated by the Sterling equation) were in reasonably close agreement. In those cases in which the results of the two methods did not agree, $\rho_{ES}$ was generally greater than $\rho_{EV}$. This was most evident in the case of $CeO_2$ ($d_{BET}$=71.3 nm) for which the value of $\rho_{ES}$ was more than twice that of $\rho_{EV}$. To the best of our knowledge this is also the first indirect validation of the Sterling equation, which in turn may be employed to correct the standard AUC evaluation with specific respect to the fractal morphology of ENM agglomerates. Although the data presented herein suggest that for most metal oxide ENMs the estimation of density using the Sterling equation may be sufficiently accurate, it should be noted that where there was a close correspondence between $\rho_{ES}$ and $\rho_{EV}$ it was dependent upon a specific choice of fractal dimension (2.3), which is slightly larger than the value of 2.1 derived from scattering data and claimed as universally valid for reaction-limited colloidal agglomeration (Lin et al., 1990, Phys. Rev. A 41:2005-2020; Wohlleben, 2012, J. Nanopart. Res. 14(12): 1300).

Example 7

Deposited Fractions $f_D(t)$: Implications for In Vitro Dosimetry and Nanotoxicology Representative deposition fraction curves for $CeO_2$ ($d_{BET}$=71.3 nm), VENGES $SiO_2$ ($d_{BET}$=18.6 nm), CuO ($d_{BET}$=58 nm), and gold nanospheres ($d_H$=42.2 nm) are presented in FIGS. 1A-1D. Deposition fraction curves were derived using either the material density, estimated effective density, or measured effective density in order to illustrate the importance of effective density on particle kinetics in an in vitro system. These values were input to the ISDD model as the effective density parameter described prior in equation 2.

When agglomerates were assumed to efficiently pack with zero porosity and a density equal to that of the raw material ($\rho_p$=7.215 g/cm$^3$), the ISDD model estimated 100% of $CeO_2$ ($d_{BET}$=71.3 nm) would be delivered within 9 hours of exposure (FIG. 1B). When a fractal dimension of 2.3 and packing factor of 0.637 were assumed and the estimated effective density was used in the model ($\rho_{ES}$=5.060 g/cm$^3$), the time to deliver 100% the administered dose almost doubled (about 18 hours). When the empirically measured value for effective density was input in the model ($\rho_E$=2.172 g/cm$^3$ at SF=0.74048), it was estimated that only 58% of the administered dose would be delivered after 24 hours of exposure, the typical exposure time for an in vitro toxicity assay (FIG. 1B). Estimated deposition fractions based on the presently estimated effective densities were likewise substantially smaller than those based on either raw ENM densities or Sterling-estimated effective densities for all materials in the present panel, except for gold nanospheres which have an effective density roughly equal to their material density (FIGS. 1A-1D).

Figure 2:
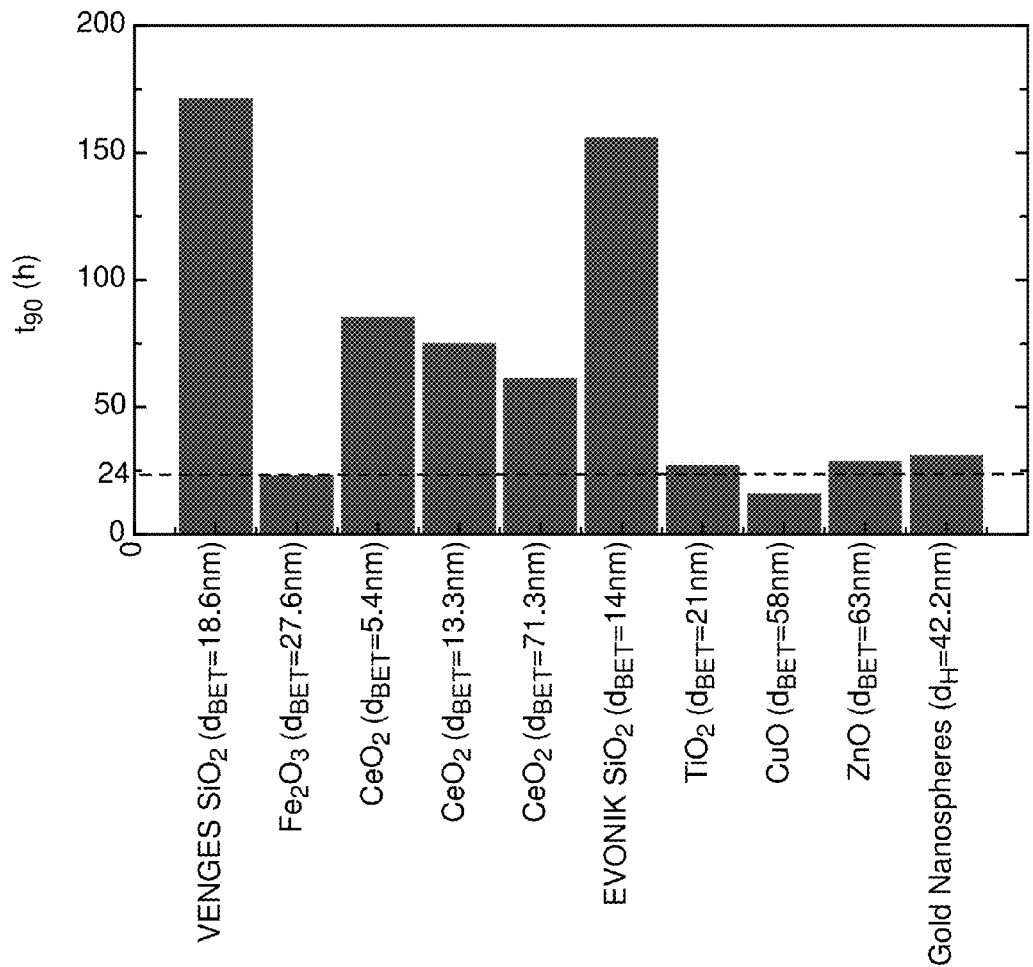
FIG. 2 is a graph illustrating the time required to deliver 90% of the administered dose to cells ($t_{90}$, hours) for various ENMs.

The time required for 90% of the administered dose to be delivered to cells in a standard 96-well plate ($t_{90}$) was estimated for each ENM based on the proposed empirically measured effective density (FIG. 2). Notably, $t_{90}$ was influenced by both ENM-specific hydrodynamic diameter and the measured effective density. Agglomerates exhibiting a relatively large hydrodynamic diameter and relatively high effective density, such as CuO ($d_H$=310 nm, $\rho_E$=1.943 g/cm$^3$) had relatively short delivery times ($t_{90}$=16 hours). Similar values were observed for Fe$_2$O$_3$ ($d_H$=380 nm, $\rho_E$=1.445 g/cm$^3$, $t_{90}$=23 hours). This pattern was distinct from that observed for materials of low hydrodynamic diameter and low effective density, such as VENGES SiO$_2$ ($d_H$=135.5 nm, $\rho_E$=1.097 g/cm$^3$, $t_{90}$=171 hours) (Tables 2 & 3, FIG. 2). FIG. 2 demonstrates the importance of proper characterization of ENM transformations in liquid suspension, as particle delivery to cells is influenced by hydrodynamic diameter, effective density, and importantly, is ENM-specific.

As a further validation, the possible error in dosimetry due to polydispersity of ENM agglomerate density was assessed. On balance between faster-settling and slower-settling agglomerates, the neglection of polydispersity by calculating with the average $d_H$ did not introduce significant errors. The systematic error in estimated dosimetry was on the order of 6%, small enough for a valid prediction of the minimal incubation time required to deliver the administered dose to the cells.

In one aspect, the findings recited herein demonstrate the accuracy and utility of the volumetric centrifugation method for estimation of ENM effective density in suspension and its use in approximating in vitro dosimetry in nanotoxicology. Effective density estimated by this method may be used to accurately determine the agglomerate state and rate of ENM agglomerate deposition and thus the delivered dose of ENM in an in vitro system. Since the cellular response to a biologically active substance that is redistributed by mass transport over time should relate more closely to the quantity of the substance coming into contact with cells than to its transient initial distribution (e.g., administered mass concentration), nanotoxicity in an in vitro system may be better represented in relation to the mean delivered dose based on accurate modeling of mass transport, than to the initial concentration of an ENM. Evaluation of cytotoxicity based on delivered dose calculations, derived from accurate characterization of ENM properties in suspension, most particularly effective density and agglomerate size, may thus help to eliminate the disparity between in vitro and in vivo nanotoxicology outcomes, which in turn could finally enable the kind of efficient and reliable screening methods needed to assess the safety of an ever-increasing number and variety of new ENMs being introduced. Moreover, the simplicity of the present method enables nanotoxicologists to incorporate more accurate dosimetry modeling in their in vitro system designs, and help them to develop predictive strategies for nanomaterial development.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of determining the effective density of a nanomaterial agglomerate in a liquid, the method comprising:
   providing a dispersion of a first mass of a nanomaterial in a liquid, wherein a nanomaterial agglomerate is present within the dispersion;
   centrifuging the dispersion at a speed sufficient to yield a supernatant and a pellet, wherein the pellet comprises a fraction of the nanomaterial agglomerate;
   measuring the volume of the pellet and the mass of the nanomaterial left in the supernatant; and,
   calculating the effective density of the nanomaterial agglomerate ($\rho_E$) by applying the formula:

$$\rho_E = \frac{\rho_{media} V_{pellet} SF + \left[\left(1 - \frac{\rho_{media}}{\rho_{ENM}}\right) \times (M_{ENM} - M_{ENMsn})\right]}{V_{pellet} SF},$$

wherein:
   $\rho_{media}$ is the density of the liquid;
   $V_{pellet}$ is the measured volume of the pellet;
   SF is the stacking factor for the nanomaterial;
   $\rho_{ENM}$ is the density of the nanomaterial;
   $M_{ENM}$ is the first mass of nanomaterial;
   $M_{ENMsn}$ is the measured mass of nanomaterial left in the supernatant;
thus determining the effective density of the nanomaterial agglomerate.

2. The method of claim 1, wherein the speed of centrifugation is equal to or less than about 6,000×g.

3. The method of claim 2, wherein the speed of centrifugation is equal to or less than about 2,000×g.

4. The method of claim 1, wherein the dispersion is centrifuged for about 3 hours or less.

5. The method of claim 4, wherein the dispersion is centrifuged for about 1 hour or less.

6. The method of claim 1, wherein the mass of nanomaterial agglomerate is greater in the pellet than in the supernatant.

7. The method of claim 6, wherein the ratio of mass of nanomaterial agglomerate in the pellet and the supernatant is equal to or greater than about 96:4.

8. The method of claim 1, wherein the nanoparticles stack as tight ordered spheres in the pellet.

9. The method of claim 8, wherein the stacking factor for the nanoparticles is about 0.74048.

10. The method of claim 1, wherein the liquid comprises a biological fluid.

* * * * *

UNITED STATES PATENT AND TRADEMARK OFFICE
CERTIFICATE OF CORRECTION

PATENT NO. : 9,360,408 B2
APPLICATION NO. : 14/407649
DATED : June 7, 2016
INVENTOR(S) : Demokritou et al.

Page 1 of 1

It is certified that error appears in the above-identified patent and that said Letters Patent is hereby corrected as shown below:

In the Specification

Delete the paragraph beginning at Column 1, Line number 19, and replace it with the following paragraph:
This invention was made with government support under ES000002 awarded by the National Institutes of Health. The government has certain rights in the invention.

Signed and Sealed this
Twenty-first Day of January, 2025

Coke Morgan Stewart
*Acting Director of the United States Patent and Trademark Office*